United States Patent
Kao

(10) Patent No.: US 9,301,864 B2
(45) Date of Patent: *Apr. 5, 2016

(54) BI-DIRECTIONAL STENT DELIVERY SYSTEM

(75) Inventor: Stephen Kao, Sunnyvale, CA (US)

(73) Assignee: VENITI, INC., Fremont, CA (US)

(*) Notice: Subject to any disclaimer, the term of this patent is extended or adjusted under 35 U.S.C. 154(b) by 500 days.

This patent is subject to a terminal disclaimer.

(21) Appl. No.: 13/156,327

(22) Filed: Jun. 8, 2011

(65) Prior Publication Data

US 2011/0307049 A1 Dec. 15, 2011

Related U.S. Application Data

(63) Continuation-in-part of application No. 12/911,604, filed on Oct. 25, 2010, now Pat. No. 8,864,811.

(60) Provisional application No. 61/352,408, filed on Jun. 8, 2010.

(51) Int. Cl.
*A61F 2/06* (2013.01)
*A61F 2/966* (2013.01)
*A61F 2/95* (2013.01)

(52) U.S. Cl.
CPC .......... *A61F 2/966* (2013.01); *A61F 2002/9505* (2013.01); *A61F 2002/9517* (2013.01); *A61F 2002/9665* (2013.01); *A61F 2220/0025* (2013.01)

(58) Field of Classification Search
CPC . A61F 2/962; A61F 2/966; A61F 2002/9517; A61F 2002/9665
USPC ............................................... 623/1.11, 1.12
See application file for complete search history.

(56) References Cited

U.S. PATENT DOCUMENTS 4,553,545 A 11/1985 Maass et al.
4,760,849 A 8/1988 Kropf
(Continued)

FOREIGN PATENT DOCUMENTS

EP 0221570 B1 1/1991
EP 0335341 B1 3/1992
(Continued)

OTHER PUBLICATIONS

Boston Scientific Corp.; Ultraflex} Tracheobronchial Stent System (product info.); retrieved from: <http://www.bostonscientific.com/templatedata/imports/collateral/PulmonaryEndoscopy/prospec_ultrfxtb_01_us.pdf>; 2 pgs.; © 2007 (year of publication is sufficiently earlier than the effective U.S. filed and any foreign priority date).

(Continued)

*Primary Examiner* — Diane Yabut
(74) *Attorney, Agent, or Firm* — Oliff PLC

(57) ABSTRACT

A bi-directional stent delivery system includes an inner elongate shaft, a radially expandable prosthesis disposed over the inner elongate shaft, an outer elongate shaft, and a shuttle sheath disposed over the radially expandable prosthesis. The distal portion of the inner shaft is releasably coupled to the distal portion of the shuttle sheath, and the distal portion of the outer shaft is releasably coupled the proximal portion of the shuttle sheath. Distal advancement of the inner shaft advances the shuttle sheath distally when the outer shaft is uncoupled from the shuttle sheath, thereby allowing the prosthesis to radially expand from a proximal end to a distal end. Proximal retraction of the outer shaft retracts the shuttle sheath proximally when the inner shaft is uncoupled from the shuttle sheath, thereby allowing the prosthesis to radially expand from a distal end to a proximal end thereof.

70 Claims, 33 Drawing Sheets

(56) References Cited

U.S. PATENT DOCUMENTS

| | | | |
|---|---|---|---|
| 5,102,417 A | 4/1992 | Palmaz | |
| 5,195,984 A | 3/1993 | Schatz | |
| 5,201,757 A * | 4/1993 | Heyn et al. | 606/198 |
| 5,275,622 A | 1/1994 | Lazarus et al. | |
| 5,292,321 A | 3/1994 | Lee | |
| 5,443,500 A | 8/1995 | Sigwart | |
| 5,449,373 A | 9/1995 | Pinchasik et al. | |
| 5,449,382 A | 9/1995 | Dayton | |
| 5,451,233 A | 9/1995 | Yock | |
| 5,545,210 A | 8/1996 | Hess et al. | |
| 5,591,197 A | 1/1997 | Orth et al. | |
| 5,603,698 A | 2/1997 | Roberts et al. | |
| 5,649,949 A | 7/1997 | Wallace et al. | |
| 5,669,932 A | 9/1997 | Fischell et al. | |
| 5,693,085 A | 12/1997 | Buirge et al. | |
| 5,733,303 A | 3/1998 | Israel et al. | |
| 5,743,873 A | 4/1998 | Cai et al. | |
| 5,755,776 A | 5/1998 | Al Saadon | |
| 5,755,781 A | 5/1998 | Jayaraman | |
| 5,776,142 A | 7/1998 | Gunderson | |
| 5,792,165 A * | 8/1998 | Klieman et al. | 606/170 |
| 5,810,872 A | 9/1998 | Kanesaka et al. | |
| 5,836,964 A | 11/1998 | Richter et al. | |
| 5,873,907 A | 2/1999 | Frantzen | |
| 5,893,887 A | 4/1999 | Jayaraman | |
| 5,902,333 A | 5/1999 | Roberts et al. | |
| 5,907,893 A | 6/1999 | Zadno Azizi et al. | |
| 5,919,204 A | 7/1999 | Lukic et al. | |
| 5,925,061 A | 7/1999 | Ogi et al. | |
| 5,954,743 A | 9/1999 | Jang | |
| 6,042,597 A | 3/2000 | Kveen et al. | |
| 6,090,127 A | 7/2000 | Globerman | |
| 6,129,755 A | 10/2000 | Mathis et al. | |
| 6,193,745 B1 | 2/2001 | Fogarty et al. | |
| 6,241,757 B1 | 6/2001 | An et al. | |
| 6,254,612 B1 | 7/2001 | Hieshima | |
| 6,261,318 B1 | 7/2001 | Lee et al. | |
| 6,264,690 B1 | 7/2001 | Von Oepen | |
| 6,352,552 B1 | 3/2002 | Levinson et al. | |
| 6,468,299 B2 | 10/2002 | Stack et al. | |
| 6,562,064 B1 | 5/2003 | deBeer | |
| 6,579,308 B1 | 6/2003 | Jansen et al. | |
| 6,585,758 B1 | 7/2003 | Chouinard et al. | |
| 6,599,314 B2 | 7/2003 | Mathis | |
| 6,602,281 B1 | 8/2003 | Klein | |
| 6,605,110 B2 | 8/2003 | Harrison | |
| 6,656,220 B1 | 12/2003 | Gomez et al. | |
| 6,682,554 B2 | 1/2004 | Oepen et al. | |
| 6,699,278 B2 | 3/2004 | Fischell et al. | |
| 6,716,238 B2 | 4/2004 | Elliott | |
| 6,749,629 B1 | 6/2004 | Hong et al. | |
| 6,761,731 B2 | 7/2004 | Majercak | |
| 6,776,793 B2 | 8/2004 | Brown et al. | |
| 6,799,357 B2 | 10/2004 | Webb et al. | |
| 6,849,084 B2 * | 2/2005 | Rabkin et al. | 623/1.12 |
| 6,878,162 B2 | 4/2005 | Bales et al. | |
| 6,929,660 B1 | 8/2005 | Ainsworth et al. | |
| 6,955,688 B2 | 10/2005 | Wilson et al. | |
| 7,018,401 B1 | 3/2006 | Hyodoh et al. | |
| 7,122,049 B2 | 10/2006 | Banas et al. | |
| 7,131,993 B2 | 11/2006 | Gregorich | |
| 7,137,993 B2 | 11/2006 | Acosta et al. | |
| 7,163,553 B2 | 1/2007 | Limon | |
| 7,252,679 B2 | 8/2007 | Fischell et al. | |
| 7,344,560 B2 | 3/2008 | Gregorich et al. | |
| 7,520,890 B2 | 4/2009 | Phillips | |
| 7,556,644 B2 | 7/2009 | Burpee | |
| 7,594,927 B2 | 9/2009 | Majercak et al. | |
| 7,611,531 B2 | 11/2009 | Calisse | |
| 7,722,661 B2 | 5/2010 | Lenz et al. | |
| 8,317,859 B2 | 11/2012 | Snow et al. | |
| 8,337,546 B2 * | 12/2012 | Bruszewski | 623/1.35 |
| 2001/0044650 A1 | 11/2001 | Simso et al. | |
| 2002/0045935 A1 | 4/2002 | Jang | |
| 2002/0082682 A1 | 6/2002 | Barclay et al. | |
| 2002/0120323 A1 | 8/2002 | Thompson et al. | |
| 2003/0040771 A1 | 2/2003 | Hyodoh et al. | |
| 2003/0097172 A1 | 5/2003 | Shalev et al. | |
| 2003/0109887 A1 | 6/2003 | Galdonik et al. | |
| 2003/0114920 A1 | 6/2003 | Caro et al. | |
| 2003/0130726 A1 | 7/2003 | Thorpe et al. | |
| 2003/0195609 A1 | 10/2003 | Berenstein et al. | |
| 2004/0006381 A1 | 1/2004 | Sequin et al. | |
| 2004/0088044 A1 | 5/2004 | Brown et al. | |
| 2004/0147997 A1 * | 7/2004 | Gittings | 623/1.11 |
| 2004/0158247 A1 * | 8/2004 | Sitiso et al. | 606/61 |
| 2004/0158312 A1 | 8/2004 | Chouinard et al. | |
| 2004/0167609 A1 | 8/2004 | Majercak | |
| 2004/0186556 A1 | 9/2004 | Hogendijk et al. | |
| 2004/0186560 A1 | 9/2004 | Alt | |
| 2004/0204752 A1 | 10/2004 | Ehr et al. | |
| 2004/0220585 A1 | 11/2004 | Nikolchev | |
| 2005/0015136 A1 | 1/2005 | Ikeuchi et al. | |
| 2005/0049667 A1 | 3/2005 | Arbefeuille et al. | |
| 2005/0055080 A1 | 3/2005 | Istephanous et al. | |
| 2005/0107863 A1 | 5/2005 | Brown | |
| 2005/0131516 A1 | 6/2005 | Greenhalgh | |
| 2005/0288764 A1 * | 12/2005 | Snow et al. | 623/1.11 |
| 2006/0020322 A1 | 1/2006 | Leynov et al. | |
| 2006/0074474 A1 | 4/2006 | Theron | |
| 2006/0106452 A1 | 5/2006 | Niermann | |
| 2006/0116751 A1 | 6/2006 | Bayle et al. | |
| 2006/0142849 A1 | 6/2006 | Killion et al. | |
| 2006/0247759 A1 | 11/2006 | Burpee et al. | |
| 2007/0055348 A1 | 3/2007 | Pryor | |
| 2007/0129786 A1 | 6/2007 | Beach et al. | |
| 2007/0185563 A1 | 8/2007 | Zarbatany et al. | |
| 2007/0219618 A1 | 9/2007 | Cully et al. | |
| 2007/0255387 A1 | 11/2007 | Kramer et al. | |
| 2008/0103584 A1 | 5/2008 | Su et al. | |
| 2008/0109068 A1 | 5/2008 | Fischell et al. | |
| 2008/0125849 A1 | 5/2008 | Burpee et al. | |
| 2008/0208319 A1 | 8/2008 | Rabkin et al. | |
| 2008/0215129 A1 | 9/2008 | Venturelli et al. | |
| 2008/0294230 A1 * | 11/2008 | Parker | 623/1.11 |
| 2008/0294240 A1 | 11/2008 | Casey | |
| 2008/0306581 A1 | 12/2008 | Berglund et al. | |
| 2009/0024205 A1 | 1/2009 | Hebert et al. | |
| 2009/0036976 A1 | 2/2009 | Beach et al. | |
| 2009/0099592 A1 * | 4/2009 | Buiser et al. | 606/200 |
| 2009/0118810 A1 | 5/2009 | Klein et al. | |
| 2009/0163989 A1 | 6/2009 | Contiliano et al. | |
| 2009/0182407 A1 | 7/2009 | Leanna et al. | |
| 2009/0210049 A1 | 8/2009 | Thielen et al. | |
| 2009/0264978 A1 | 10/2009 | Dieck et al. | |
| 2010/0004730 A1 * | 1/2010 | Benjamin et al. | 623/1.11 |
| 2010/0023106 A1 * | 1/2010 | Meyer et al. | 623/1.11 |
| 2010/0057187 A1 | 3/2010 | Caldarise et al. | |
| 2010/0137973 A1 | 6/2010 | Sutermeister et al. | |
| 2010/0294287 A1 | 11/2010 | Raju et al. | |
| 2011/0106237 A1 | 5/2011 | Bonsignore et al. | |
| 2011/0230957 A1 | 9/2011 | Bonsignore et al. | |
| 2011/0301685 A1 | 12/2011 | Kao | |
| 2012/0078341 A1 | 3/2012 | Kao | |
| 2012/0078344 A1 | 3/2012 | Kao | |

FOREIGN PATENT DOCUMENTS

| | | |
|---|---|---|
| EP | 1304091 A2 | 4/2003 |
| JP | 2008-504078 A | 2/2008 |
| WO | WO 98/38945 A1 | 9/1998 |
| WO | WO 00/16718 A1 | 3/2000 |
| WO | WO 00/28922 A1 | 5/2000 |
| WO | WO 00/57813 A1 | 10/2000 |
| WO | WO 03/051425 A2 | 6/2003 |
| WO | WO 2005/030093 A1 | 4/2005 |
| WO | 2006/005082 A2 | 1/2006 |

(56) References Cited

FOREIGN PATENT DOCUMENTS

| WO | 2007/098232 A2 | 8/2007 |
|----|----------------|--------|
| WO | WO 2007/092276 A2 | 8/2007 |
| WO | WO 2007/098232 A2 | 8/2007 |

OTHER PUBLICATIONS

Duerig et al.; An overview of superelastic stent design; Min Invas Ther & Allied Technol; vol. 9(3/4); pp. 235-246; (year of publication is sufficiently earlier than the effective U.S. filed and any foreign priority date) 2000.

Malvé et al.; FSI analysis of the coughing mechanism in a human trachea; Annals of Biomedical Engineering; vol. 38; No. 4; pp. 1556-1565; Apr. 2010.

Raju et al.; U.S. Appl. No. 11/944,094 entitled "Venous Stent," filed Nov. 21, 2007.

Raju et al.; U.S. Appl. No. 12/903,056 entitled "Venous Stent," filed Oct. 12, 2010.

Raju; U.S. Appl. No. 12/603,970 entitled "Venous Stent," filed Oct. 22, 2009.

Supplementary European Search Report, Veniti, Inc., Application No. 11793126.1-1506 / 2579822, PCT/US2011/039688, dated Apr. 14, 2014, (5 pgs.).

Jun. 19, 2015 Office Action issued in U.S. Appl. No. 14/487,923.

Sep. 2, 2014 Office Action issued in Chinese Patent Application No. 201180037918.8.

Feb. 13, 2015 Office Action issued in Chinese Patent Application No. 201180037918.8.

Mar. 24, 2015 Office Action issued in Japanese Patent Application No. 2013-514350.

\* cited by examiner

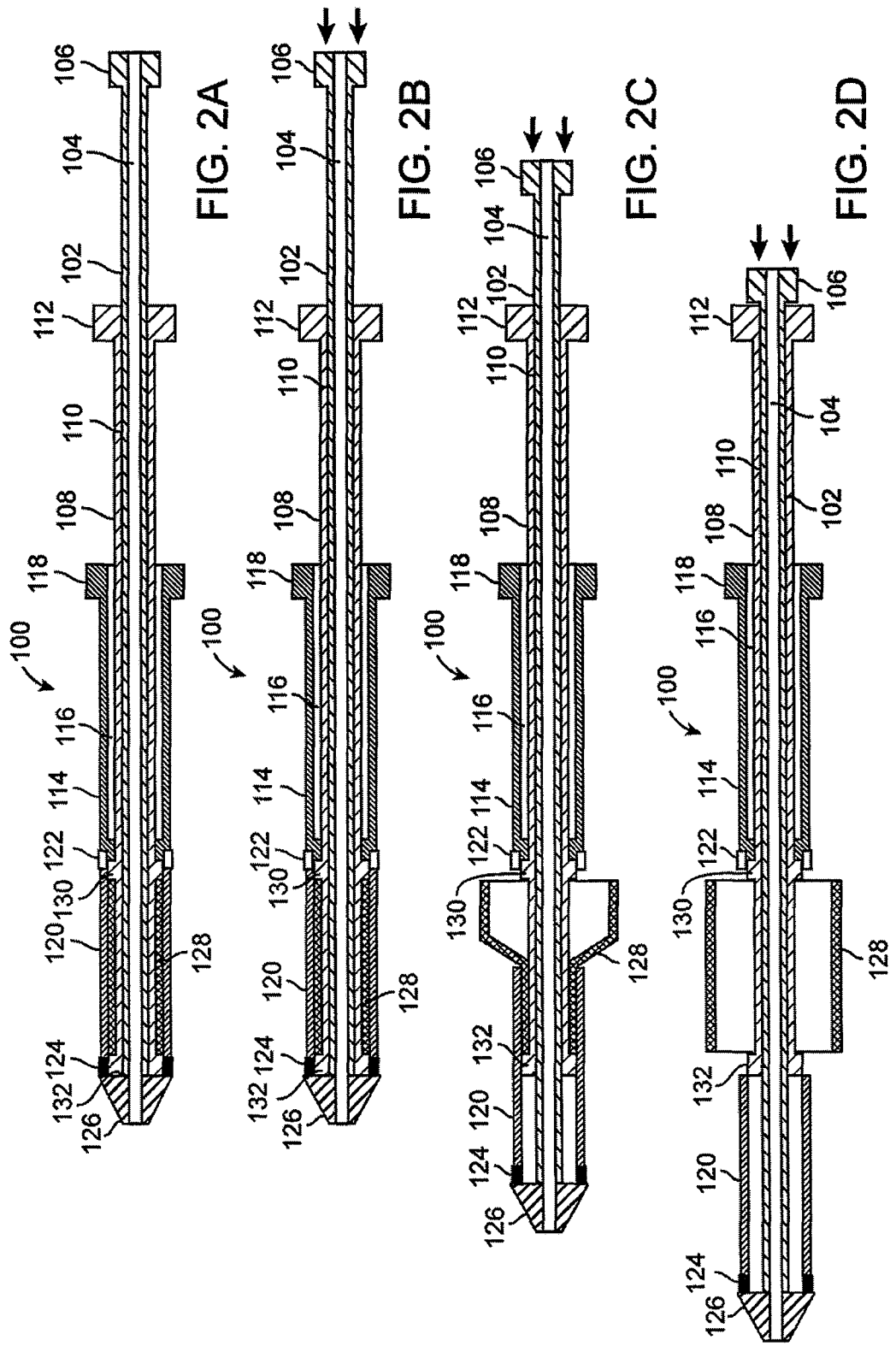

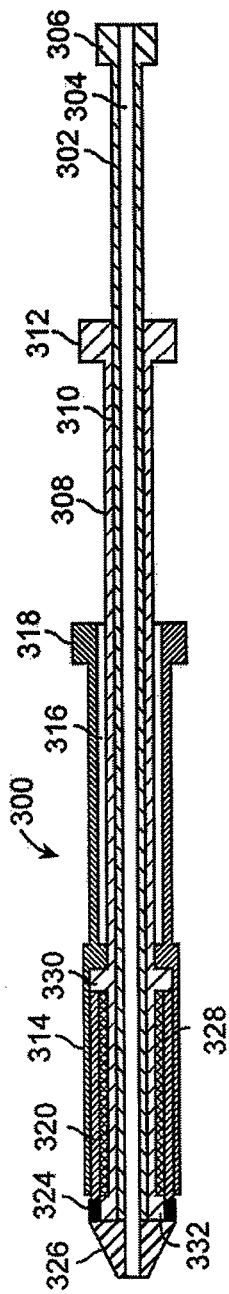
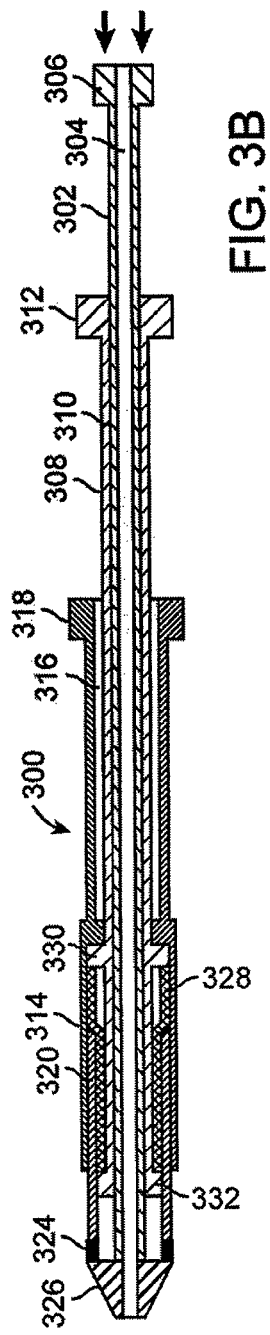
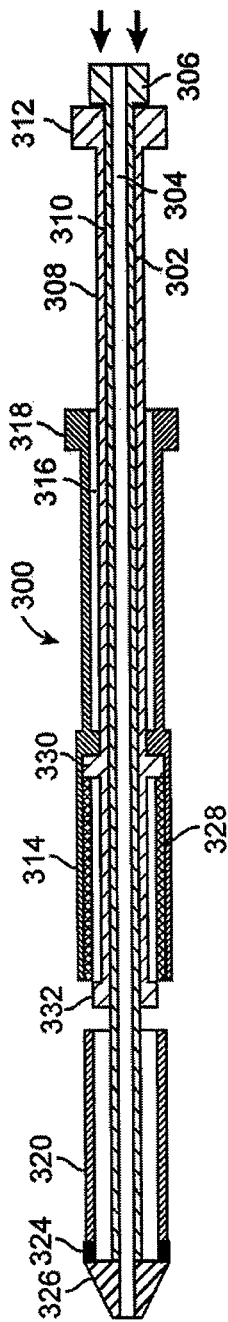
FIG. 3A
FIG. 3B
FIG. 3C

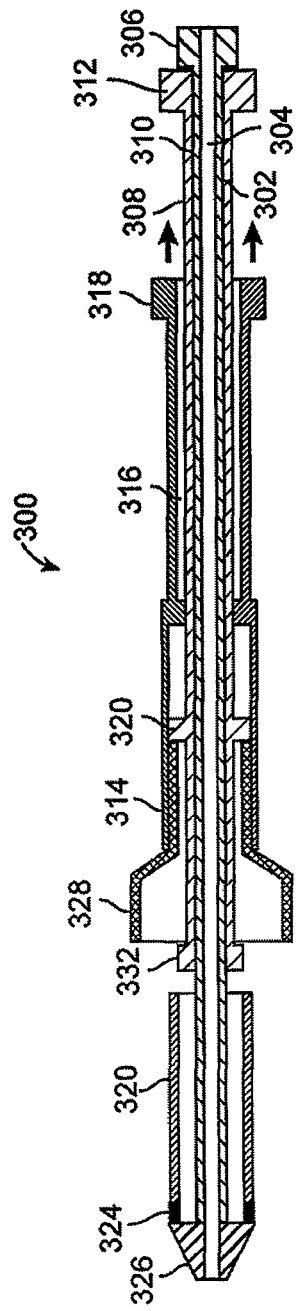
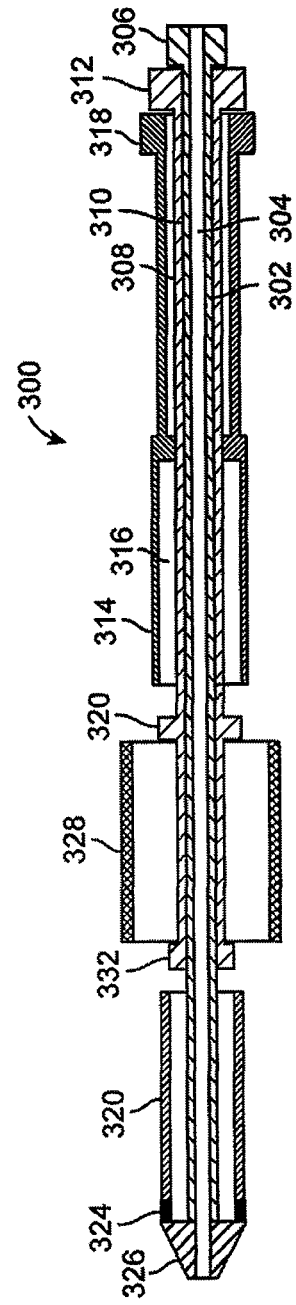
FIG. 3D
FIG. 3E

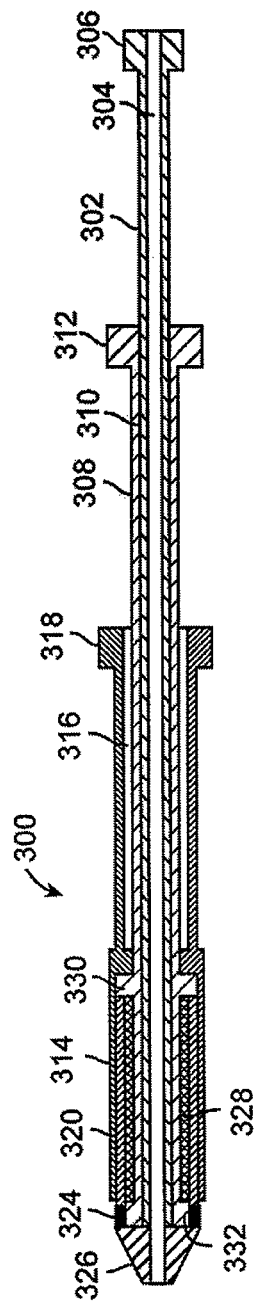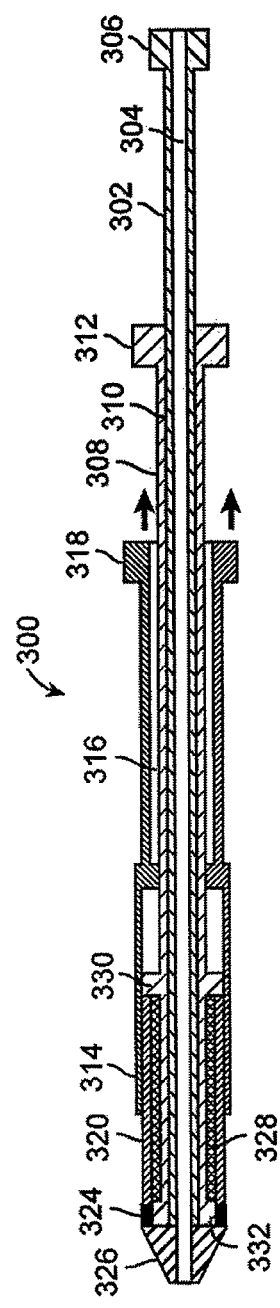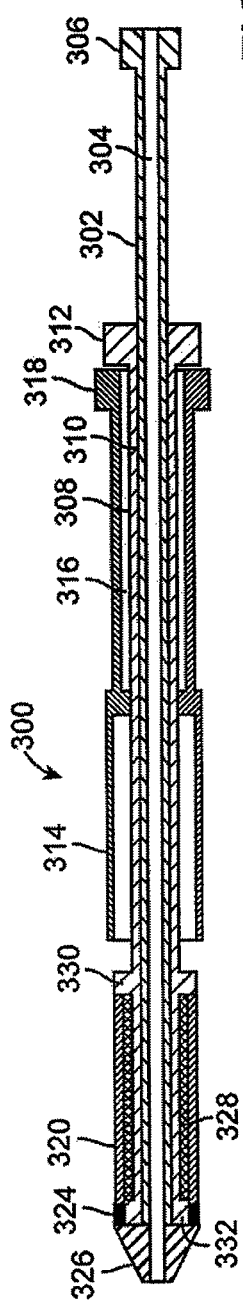
FIG. 4A
FIG. 4B
FIG. 4C

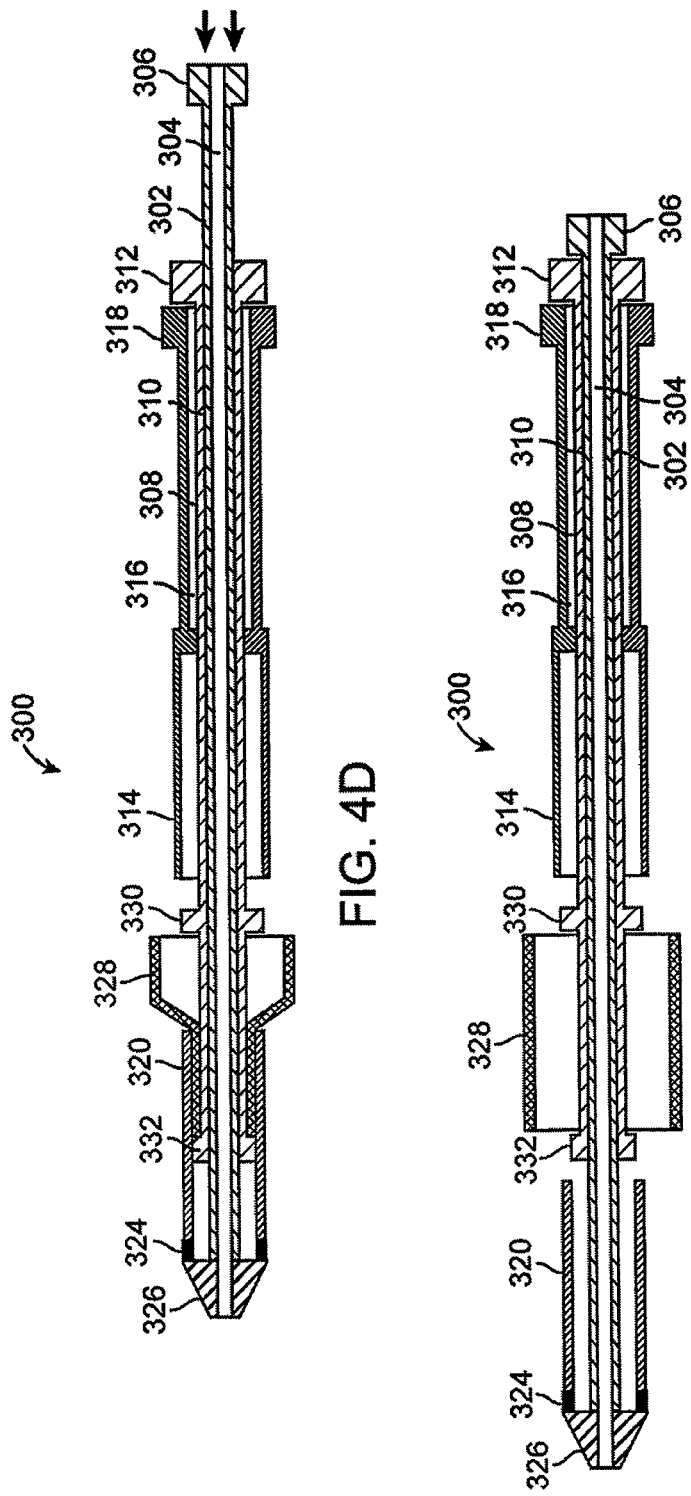

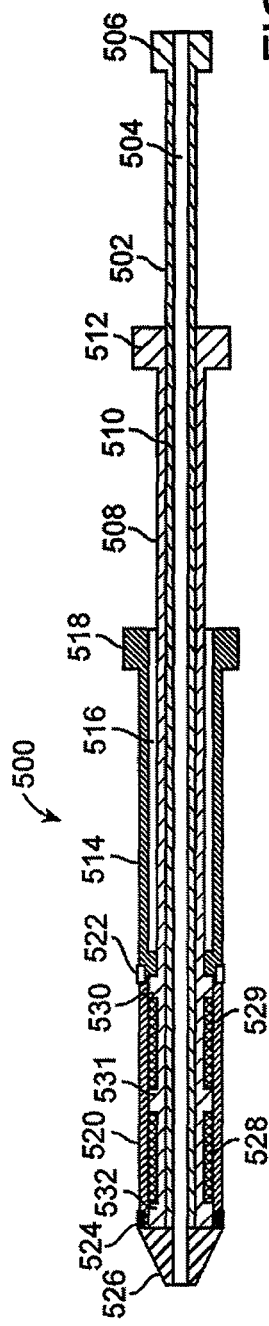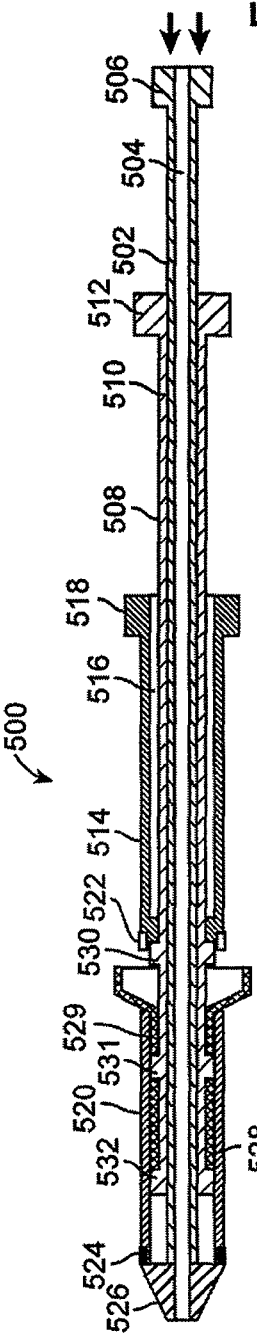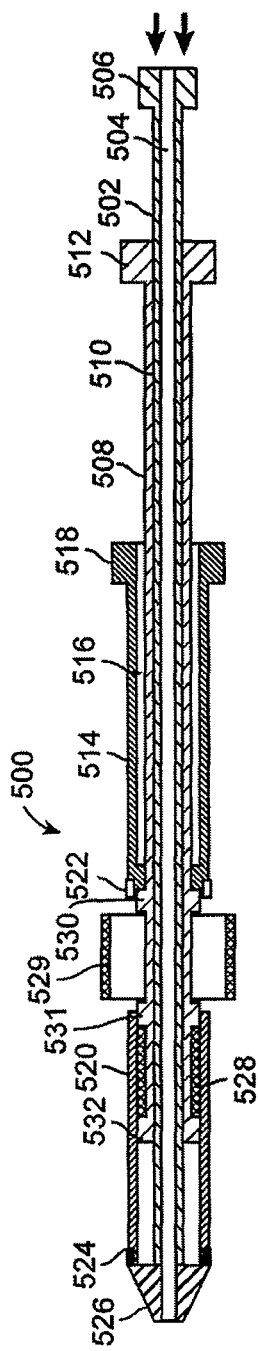

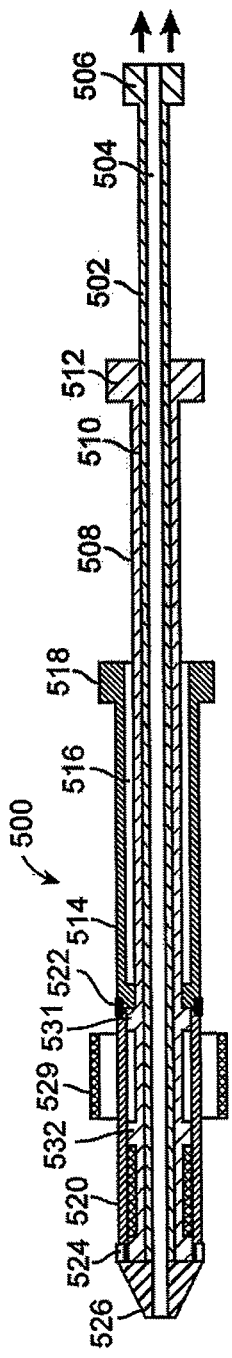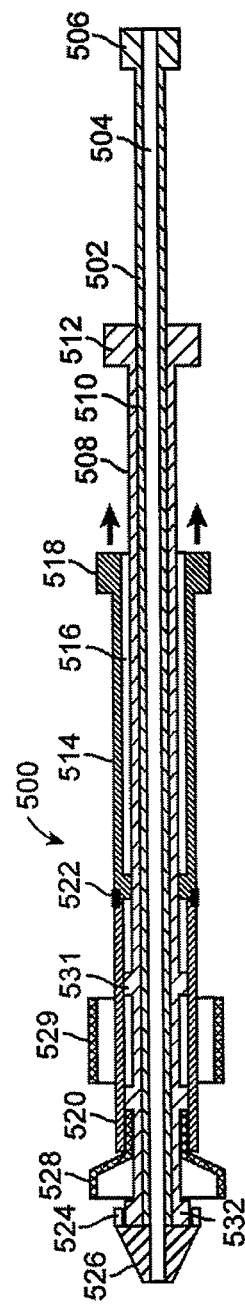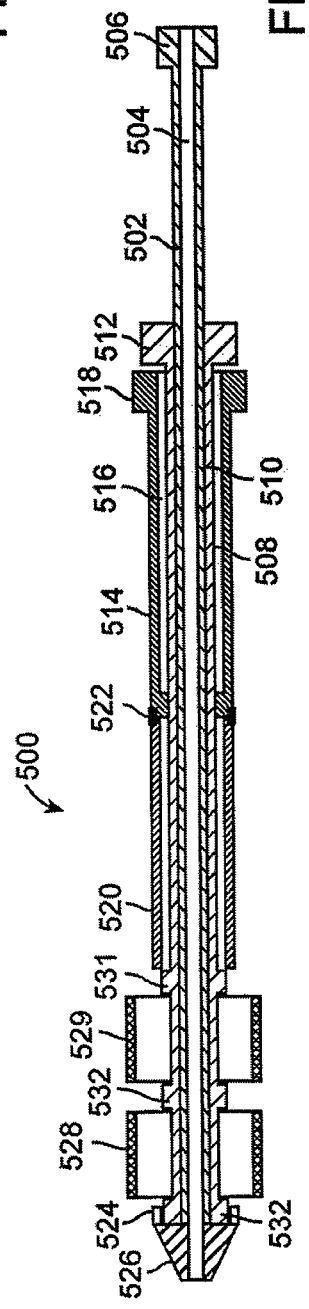

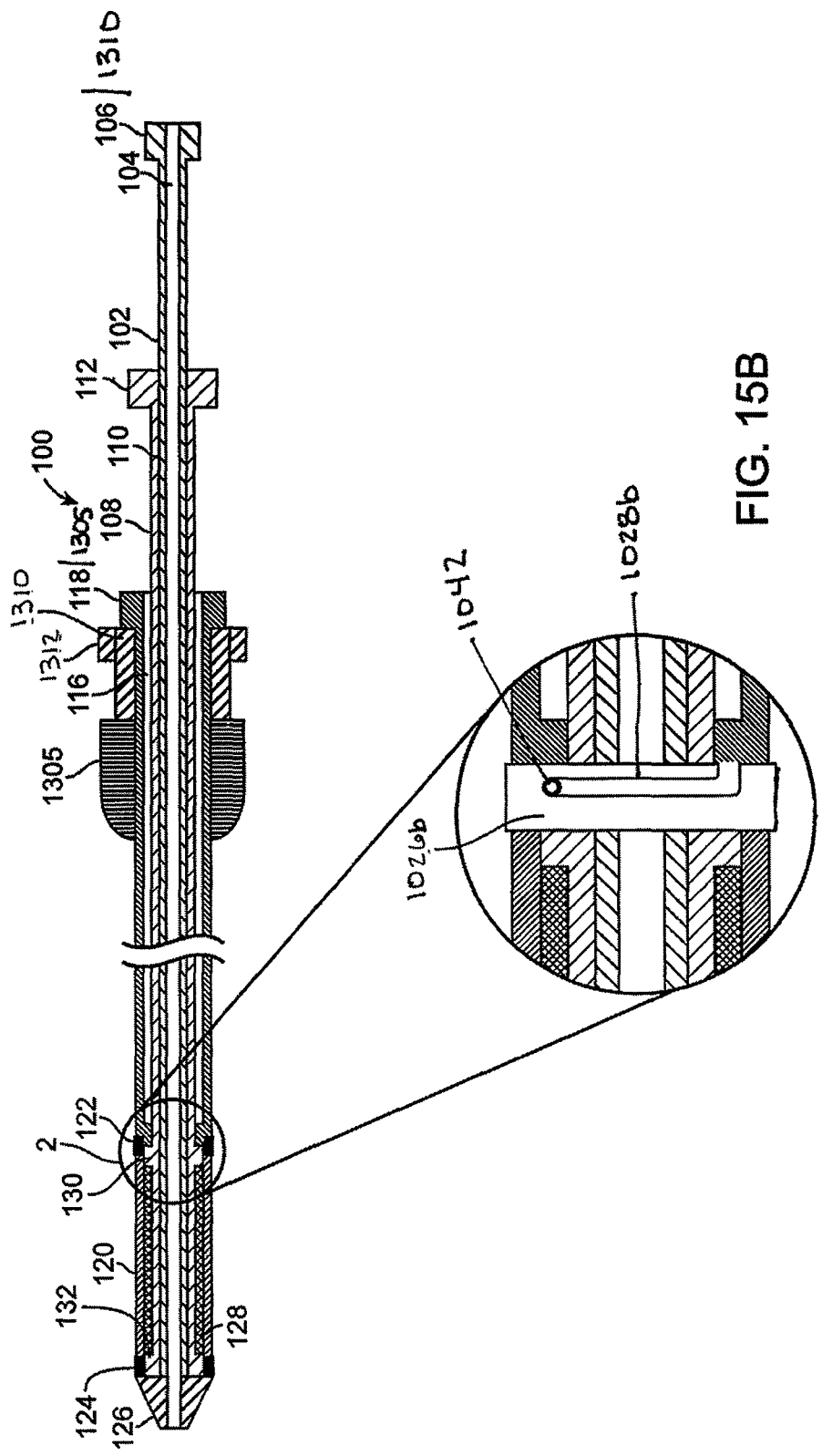

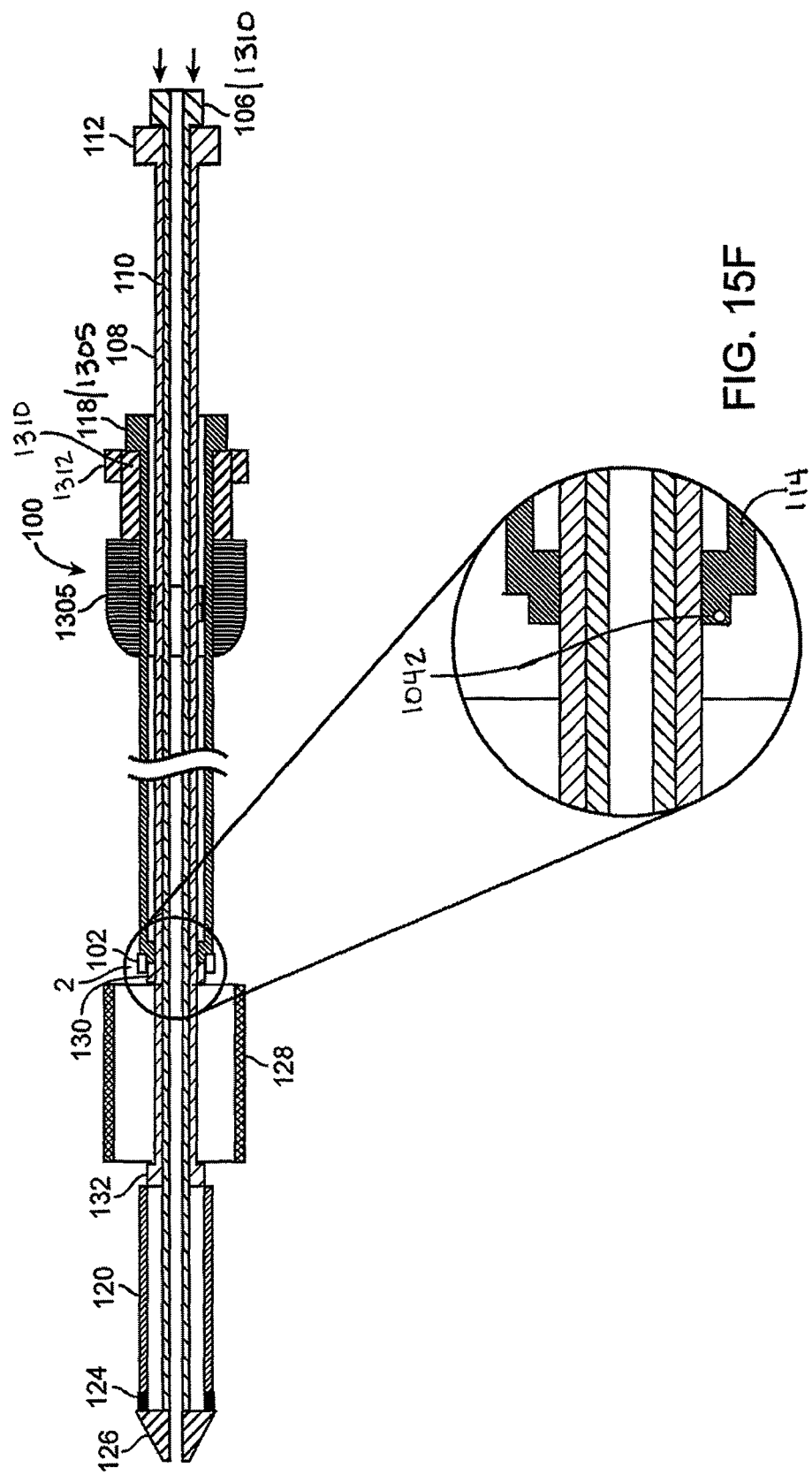

BI-DIRECTIONAL STENT DELIVERY SYSTEM

CROSS REFERENCE TO RELATED APPLICATIONS

The present application is a continuation-in-part of U.S. patent application Ser. No. 12/911,604, filed Oct. 25, 2010, now U.S. Pat. No. 8,864,811, which claims the benefit of U.S. Provisional Patent Application No. 61/352,408, filed Jun. 8, 2010, the entire contents of both application are incorporated herein by reference.

BACKGROUND OF THE INVENTION

1. Field of the Invention

The present invention relates generally to medical devices, and more particularly to endoluminal delivery systems for prostheses such as stents, or other implantable structures. The delivery systems may be used for placement of a stent in the arterial system, the venous system, or any other portion of the body. The use of stents and other implantable medical devices such as grafts, stent-grafts, filters, shunts, valves, etc., are referred to herein as prostheses. Prostheses may be used to deliver drugs to tissue, support tissue, or maintain patency of bodily lumens, as well as performing other functions, and have been widely reported in the scientific and patent literature.

Stents are typically delivered via a catheter in an unexpanded configuration to a desired location in the body. The combined stent and catheter is typically referred to as the stent delivery system. Once at the desired location, the stent is expanded and implanted into the body lumen. Examples of locations in the body include, but are not limited to, arteries (e.g. aorta, coronary, carotid, cranial, iliac, femoral, etc.), veins (e.g. vena cava, jugular, iliac, femoral, hepatic, subclavian, brachiocephalic, azygous, cranial, etc.), as well as other locations including the esophagus, biliary duct, trachea, bronchials, duodenum, colon, and ureter.

Typically, a stent will have an unexpanded configuration with reduced diameter for placement and an expanded configuration with expanded diameter after placement in the vessel, duct, or tract. Some stents are self-expanding, and some stents are mechanically expanded with a radial outward force applied from within the stent (e.g. with a balloon). Some stents have one or more characteristics common to both self-expanding and mechanically expandable stents.

Self-expanding stents are made from a material that is resiliently biased to return to a pre-set shape. These materials may include superelastic and shape memory materials that can expand to an implanted configuration upon delivery or through a change in temperature. Self-expanding stents are constructed from a wide variety of materials including nitinol (a nickel titanium alloy), spring steel, shape-memory polymers, etc.

In many stent delivery systems, particularly those used to deliver a self-expanding stent, the stent is typically retained on the catheter in its unexpanded form with a constraining member or other retention device such as a sheath or outer shaft. The stent may be deployed by retracting the outer shaft from over the stent. To prevent the stent from being drawn longitudinally with the retracting shaft, many delivery systems provide the catheter shaft with a pusher, bumper, hub, holder or other stopping element.

Precise delivery of stents can be challenging. In the case of balloon expandable stents, the stent may foreshorten as the stent radially expands, therefore, the change in length must be taken into account when deploying the stent at the treatment site. In the case of self-expanding stents, due to the elastic nature of the stents, they may "jump" away from the delivery catheter during deployment. For this reason, it would be desirable to provide improved stent delivery systems that can accurately deliver a prosthesis such as a stent to a desired treatment site. Additionally, depending on the anatomy being treated, this may add further challenges to accurate stent delivery. In certain parts of the anatomy, exact placement of the stent is critical to the successful clinical outcome of the procedure. For example, percutaneous coronary intervention (PCI) in ostial coronary artery lesions has been technically difficult because the stent is preferably precisely deployed in the ostium without side branch compromise. A similar level of accuracy is needed with ilio-femoral and ilio-caval stenting as is routinely used for the treatment of iliac vein compression syndrome (IVCS) and post-thrombotic syndrome (PTS) whereby the profunda and the inferior vena cava can be partially or completely blocked (or "stent jailed") by the stent if the stent is not placed accurately after deployment. Other examples where precise placement of the stent are important include but are not limited to any number of arterial applications, esophageal stenting of gastric varices, transjugular intrahepatic portosystemic shunt (TIPS) stenting for relief of portal hypertension, and use of endovascular stent-grafts for arterial aneurysms (e.g. AAA, femoral, popliteal).

Additionally, depending on the direction from which the delivery catheter approaches the treatment site, it may be desirable to deploy the stent in a preferred direction. Physicians may enter the body through different access sites, e.g. femoral vein or artery, the internal jugular vein (IJV), etc. before inserting the stent delivery system through the bodily lumens to the target location. Because the stent delivery system will be in different orientations depending on the physician's choice for access site, it may be necessary for the delivery system to have the correct stent release mode, such as proximal or distal release of the stent. It would therefore be advantageous for a delivery system to allow both release modes such that the operator (e.g. physician), can use the same system with either approach. With the typical commercially available stent delivery system, the operator is limited to one approach due to the distal release of the stent. Physician technique in stenting can also dictate which release is used in a procedure. For example, in the case of iliofemoral stenting with a femoral approach the user may choose to deploy and overlap multiple stents of varying sizes using proximal release such that the smaller diameter stent is placed first and the amount of overlap with the secondary stent(s) is tightly controlled.

In situations where multiple stents are delivered, it may be desirable to selectively deploy the stents. For example, abdominal aortic aneurysm (AAA) stent-grafts can be constructed of multiple components—trunk or main body, bifurcated main, main extension, limb extensions, stepped limbs, flared limbs, etc. Because each component is placed and deployed with a preferred release, one bi-directional deployment system with multiple stents, or stent grafts, or components could serve the function of numerous standard delivery systems. The deployment of the stents or components can be any combination of proximal or distal releases. This type of stenting can be useful in other areas of the body where bifurcations are present as well.

Furthermore, operators may require bi-directional deployment in cases where the target location is bookended by anatomical features that require exact stent placement of both the distal and proximal ends of the stent. Two bi-directional deployment systems may be used with one employing the distal release and the other employing the proximal release.

The non-critical ends of each of the deployed stents would overlap with each other in the middle of the target location. Without bi-directional deployment capability, an operator would face the likelihood of understenting, overstenting, or inaccurate stent placement and suboptimal results because of the inexact lengths of stent available to treat an exact length of disease. As mentioned earlier, ilio-femoral and ilio-caval stenting of the venous system may require the user to stent entirely from the confluence of the inferior vena cava to the profunda of the leg. A distal release is preferred for accurate stent deployment at the confluence, whereas a proximal release is preferred so as to avoid "stent jailing" of the profunda. In lieu of performing this procedure with two bi-directional deployment systems, another bi-directional deployment device embodiment loaded with two stents (one deployable with distal release and one deployable with proximal release) could greatly simplify this type of procedure.

Therefore, it would be desirable to deploy a stent from its distal end toward its proximal end, as is traditionally done in many conventional stent procedures. In other cases, it would be desirable if the stent could be deployed from its proximal end toward its distal end. In the case where multiple stents are deployed, it would be desirable if a first stent could be deployed in a first direction, and a second stent deployed in a second direction that may be the same or different than the first direction. Thus, improved stent delivery systems such as a bi-directional stent deployment system, also referred to as bi-modal, or selectively deployable stent delivery system would be advantageous. Additionally, since there currently are no FDA approved and commercially available stents and delivery systems for treating venous outflow obstruction, there is need for such devices and methods of use. At least some of these objectives will be met by the inventions described herein.

2. Description of the Background Art

Relevant patent applications include U.S. patent application Ser. No. 12/903,056, filed Oct. 12, 2010, the entire contents of which are incorporated herein by reference. Other relevant patents and publications include U.S. Pat. Nos. 7,137,993; 6,849,084; 6,716,238; 6,562,064; 5,873,907; and U.S. Patent Publication Nos. 2009/0264978; 2004/220585; 2002/120323; and 2002/188341.

BRIEF SUMMARY OF THE INVENTION

The present invention relates generally to medical devices, and more particularly to endoluminal delivery systems for prostheses such as stents, or other implantable structures. The delivery systems may be used for placement of a stent in the arterial system, the venous system, or any other portion of the body.

In a first aspect of the present invention, a bi-directional stent delivery system comprises an inner elongate shaft having a proximal portion and a distal portion, and a radially expandable prosthesis disposed over the inner elongate shaft. The prosthesis has a radially collapsed configuration and a radially expanded configuration. In the collapsed configuration the prosthesis is adapted to be delivered through a patient's vasculature, and in the expanded configuration the prosthesis engages a vessel wall or other tissue. An outer elongate shaft has a proximal portion and a distal portion. A shuttle sheath has a proximal portion and a distal portion. The shuttle sheath is disposed over the radially expandable prosthesis. The distal portion of the inner shaft is releasably coupled to the distal portion of the shuttle sheath, and the distal portion of the outer shaft is releasably coupled the proximal portion of the shuttle sheath. Distal advancement of the inner shaft advances the shuttle sheath distally when the outer shaft is uncoupled from the shuttle sheath, thereby allowing the prosthesis to radially expand from a proximal end thereof to a distal end thereof. Proximal retraction of the outer shaft retracts the shuttle sheath proximally when the inner shaft is uncoupled from the shuttle sheath, thereby allowing the prosthesis to radially expand from a distal end thereof to a proximal end thereof.

The inner shaft may comprise a lumen extending between the proximal and distal portions that is configured to slidably receive a guidewire. The prosthesis may comprise a first stent. A second stent may also be included with the system, and the second stent may be unattached and axially separated from the first stent by a gap. The stents may be self-expanding, balloon expandable, or a combination thereof. The stents may be fabricated from a nickel titanium alloy such as nitinol.

The outer shaft may comprise a lumen extending between the proximal and distal portions thereof. The shuttle sheath may have a length that is equal to or greater than the length of the radially expandable stent or stents. The shuttle sheath may constrain the prosthesis along substantially its entire length. The shuttle sheath may have a proximal end, a distal end, and a lumen extending therebetween. The shuttle sheath may comprise a substantially cylindrical sheath.

The system may further comprise a distal coupling mechanism that releasably couples the distal portion of the inner shaft to the distal portion of the shuttle sheath. The distal coupling mechanism may comprise a threaded or helical region on the distal portion of the inner shaft and a corresponding threaded or helical region on the distal portion of the shuttle sheath. The distal coupling mechanism may comprise one or more of a snap fit, an interference fit, a barbed connector, a locking mechanism, a rotatable key lock, a linear key lock, a threaded bushing, a twist lock, a magnetic coupling, a bayonet coupling, or a frangible connector. The system may further comprise a proximal coupling mechanism that releasably couples the distal portion of the outer shaft to the proximal portion of the shuttle sheath. The proximal coupling mechanism may comprise a threaded or helical region on the distal portion of the outer shaft and a corresponding threaded or helical region on the proximal portion of the shuttle sheath. The proximal coupling mechanism may comprise one or more of a snap fit, an interference fit, a barbed connector, a locking mechanism, a rotatable key lock, a linear key lock, a threaded bushing, a twist lock, a magnetic coupling, a bayonet coupling, or a frangible connector.

The inner shaft may be threadably or helically engaged with the shuttle sheath, and the outer shaft may also be threadably or helically engaged with the shuttle sheath. The threads or helix engaging the inner shaft with the shuttle sheath may have a first orientation, and the threads or helix engaging the outer shaft with the shuttle sheath may have a second orientation opposite of the first orientation such that rotation of the inner shaft in a first direction couples the inner shaft with the shuttle sheath and rotation of the inner shaft in a second direction opposite the first direction disengages the inner shaft from the shuttle sheath. Additionally rotation of the outer shaft in the first direction may disengage the outer shaft from the shuttle sheath and rotation of the outer shaft in the second direction may engage the outer shaft with the shuttle sheath. The inner shaft may be coupled to the shuttle sheath with a bayonet coupling mechanism that has a slot in a first orientation, and the outer shaft may be coupled with the shuttle sheath with a second bayonet coupling mechanism having a slot in a second orientation opposite the first slot.

Rotation of the inner shaft in a first direction may couple the inner shaft with the shuttle sheath and rotation of the inner shaft in a second direction opposite the first direction may disengage the inner shaft from the shuttle sheath. Rotation of the outer shaft in the first direction may disengage the outer shaft from the shuttle sheath and rotation of the outer shaft in the second direction may engage the outer shaft with the shuttle sheath.

The system may further comprise a middle shaft concentric with the inner and the outer shafts, and disposed therebetween. The prosthesis may be disposed over the middle shaft and in direct engagement therewith. The middle shaft may comprise an outer surface that is substantially smooth. The middle shaft may comprise a proximal stent stop and a distal stent stop. The proximal stop may be disposed proximally of a proximal end of the prosthesis, and the distal stopping element may be disposed distally of a distal end of the prosthesis. The proximal stopping element may prevent proximal movement of the prosthesis, and the distal stopping element may prevent distal movement of the prosthesis. The proximal stopping element or the distal stopping element may comprise one or more of a ring, a band, a step, a bushing, or a sleeve, that prevent proximal or distal movement of the prosthesis.

The system may also comprise an actuator mechanism disposed near a proximal end of the delivery system. The actuator mechanism may be operably coupled with the inner and outer shafts, thereby allowing an operator to couple and uncouple the inner and outer shafts with the shuttle sheath. The actuator mechanism may also be configured to slidably or rotatably move the inner and the outer shafts both proximally and distally. The system may further comprise an intravascular ultrasound device configured to allow visualization of the prosthesis and surrounding tissue.

In another aspect of the present invention, a bi-directional method for deploying a prosthesis at a treatment site in a patient comprises providing a delivery catheter comprising a prosthesis having a proximal end and a distal end, the prosthesis in a collapsed configuration and disposed on the delivery catheter. The prosthesis is delivered to the target treatment site, and a deployment direction for the prosthesis is selected. The deployment direction comprises radially expanding the prosthesis from the proximal end thereof to the distal end thereof, and radially expanding the prosthesis from the distal end thereof to the proximal end thereof. A constraint is removed from the prosthesis thereby permitting the prosthesis to radially expand in the selected deployment direction. The prosthesis radially expands from the collapsed configuration to an expanded configuration in the selected deployment direction so that the expanded prosthesis engages tissue at the target treatment site. The delivery catheter is withdrawn from the patient and the prosthesis is left deployed in the patient at the target treatment site.

Delivering the prosthesis may comprise advancing the delivery catheter through vasculature of the patient to the target treatment site. The delivery catheter may have a proximal end, a distal end, and a lumen therebetween. Delivering the prosthesis may comprise slidably advancing the delivery catheter over a guidewire disposed in the lumen. Delivering the prosthesis may comprise positioning the prosthesis in a vein, such as the iliac vein.

The delivery catheter may comprise an inner elongate shaft and a shuttle sheath disposed over the prosthesis. Selecting the deployment direction for the prosthesis may comprise coupling the inner elongate shaft with the shuttle sheath, distally advancing the inner elongate shaft distally thereby advancing the shuttle sheath distally away from the prosthesis, and radially expanding the prosthesis from the proximal end thereof to the distal end thereof. Coupling the inner elongate shaft with the shuttle sheath may comprise threadably or helically engaging the inner elongate shaft with the shuttle sheath or coupling them together with a bayonet coupling. The delivery catheter may further comprise an outer elongate shaft, and selecting the deployment direction may comprise decoupling the outer elongate shaft from the shuttle sheath. Decoupling the outer elongate shaft from the shuttle sheath may comprise threadably or helically disengaging the outer elongate shaft from the shuttle sheath. Decoupling may comprise releasing a bayonet coupling between the outer elongate shaft and the shuttle sheath.

The delivery catheter may comprise an outer elongate shaft and a shuttle sheath disposed over the prosthesis. Selecting the deployment direction for the prosthesis may comprise coupling the outer elongate shaft with the shuttle sheath, proximally retracting the outer elongate shaft thereby retracting the shuttle sheath proximally away from the prosthesis, and radially expanding the prosthesis from the distal end thereof to the proximal end thereof. Coupling the outer elongate shaft with the shuttle sheath may comprise threadably or helically engaging the outer elongate shaft with the shuttle sheath. Coupling may comprise coupling the inner elongate shaft and the shuttle sheath with a bayonet coupling. The delivery catheter may further comprise an inner elongate shaft, and selecting the deployment direction may comprise decoupling the inner elongate shaft from the shuttle sheath. Decoupling the inner elongate shaft from the shuttle sheath may comprise threadably or helically decoupling the inner elongate shaft from the shuttle sheath. Decoupling may comprise releasing a bayonet coupling between the outer elongate shaft and the shuttle sheath.

The delivery catheter may comprise a shuttle sheath that is disposed over the prosthesis, and removing the constraint may comprise distally advancing the shuttle sheath away from the prosthesis so that the prosthesis is unconstrained from radial expansion in a direction extending from the proximal end of the prosthesis to the distal end of the prosthesis. The delivery catheter may comprise a shuttle sheath disposed over the prosthesis, and removing the constraint may comprise proximally retracting the shuttle sheath away from the prosthesis so that the prosthesis is unconstrained from radial expansion in a direction extending from the distal end of the prosthesis to the proximal end of the prosthesis.

Radially expanding the prosthesis may comprise self-expanding a stent. Withdrawing the delivery catheter from the patient may comprise withdrawing the delivery catheter from the patient's vasculature. The prosthesis may comprises two prostheses, and the method may comprise selecting a first deployment direction for the first prosthesis, radially expanding the first prosthesis in the first deployment direction, and radially expanding the second prosthesis in a second deployment direction opposite of the first deployment direction. The method may comprise visualizing the expanded prosthesis with various techniques including ultrasound or fluoroscopy. The method may also comprise retracting the radially expanded prosthesis into a shuttle sheath, repositioning the prosthesis, and radially expanding the prosthesis. The radially expanded prosthesis may be dilated with an expandable member such as a balloon.

These and other embodiments are described in further detail in the following description related to the appended drawing figures.

BRIEF DESCRIPTION OF THE DRAWINGS

FIGS. 2A-2D illustrate the embodiment of FIGS. 1A-1D configured for proximal stent release.

FIGS. 3A-3E illustrate an exemplary embodiment of a bi-directional stent delivery catheter configured for distal stent release.

FIGS. 4A-4E illustrate the embodiment of FIGS. 3A-3E configured for proximal stent release.

FIGS. 5A-5F illustrate an exemplary embodiment of a bi-directional stent delivery catheter for delivery of multiple stents.

FIGS. 15A-15F illustrate an exemplary embodiment of a bi-directional stent delivery catheter configured for and demonstrating a proximal stent release though use of the elements of a handle similar to that of FIG. 13.

DETAILED DESCRIPTION OF THE INVENTION

The present invention relates generally to medical devices, and more particularly to endoluminal delivery systems for prostheses such as stents, or other implantable structures. The delivery systems may be used for placement of a stent in the arterial system, the venous system, or any other portion of the body. The use of stents and other implantable medical devices such as grafts, stent-grafts, filters, shunts, valves, etc., are referred to herein as prostheses. Prostheses may be used to deliver drugs to tissue, support tissue, or maintain patency of bodily lumens, as well as performing other functions, and have been widely reported in the scientific and patent literature.

FIGS. 1A-1D and FIGS. 2A-2D illustrate a first exemplary embodiment of a bi-directional delivery system for a prosthesis. Delivery of a stent will be described, however, one of skill in the art will appreciate that the system may be used to deliver other prosthesis such as grafts, stent grafts, filters, etc. FIGS. 1A-1D illustrate distal release of a stent where the stent is deployed such that the stent expands from its distal end toward its proximal end. FIGS. 2A-2D illustrate proximal release of a stent where the stent is deployed such that the stent expands from is proximal end toward its distal end.

Figure 1A:
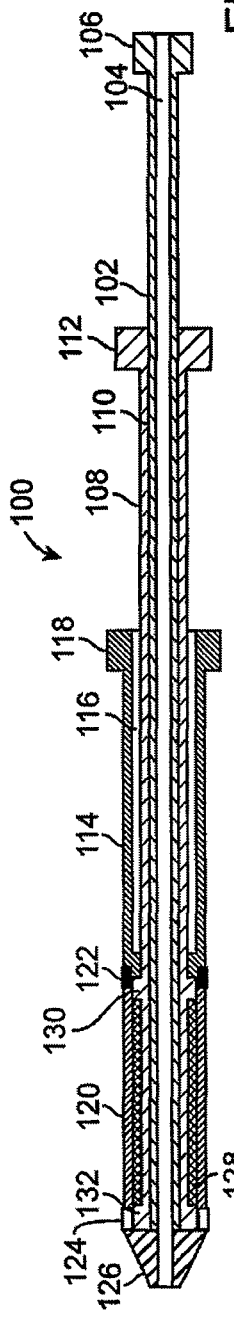
FIGS. 1A-1D illustrate an exemplary embodiment of a bi-directional stent delivery catheter configured for distal stent release.

FIG. 1A illustrates a stent delivery system 100 which is configured to preferentially deploy a stent distally. The delivery system 100 includes an inner shaft 102, a middle shaft 108, and outer shaft 114, a shuttle sheath 120 and a stent 128.

The shafts may be extruded tubes preferably having circular cross sections, or other cross sections are contemplated such as oval, rectangular, elliptical, etc. The shafts in this and other embodiments described below may be fabricated from polyethylene, PTFE, FEP, PVC, or other materials known in the art. The inner shaft 102 has a central lumen extending from its proximal end to its distal end for fluids such as contrast media or for slidably receiving a guidewire (not illustrated). A distal tapered nosecone 126 is coupled with inner shaft 102 and prevents trauma to the vessel or other tissue during delivery. A hub 106 or flared region provides the user a region for grasping, and also provides a stop for preventing the inner shaft from being advanced too far distally into the middle shaft 108 (or retracting the middle shaft too far proximally). The middle shaft 108 also has a central lumen 110 extending between its proximal and distal ends, and the middle shaft 108 is slidably disposed over the inner shaft 102. The middle shaft 108 also has a hub 112 or flared region that provides the user a region for grasping, as well as providing a stop to prevent the middle shaft 108 from being advanced too far distally into the outer shaft 114 (or retracting the outer shaft 114 too far proximally). The middle shaft 108 is slidably disposed over the inner shaft 102, and slidably disposed in the outer shaft 114 and also slidably disposed in the shuttle sheath 120. This embodiment and others described below are configured for over the wire use, although one of skill in the art will appreciate that the delivery catheters may easily be modified to allow rapid exchange use with a guidewire. Rapid exchange and over the wire use are well described in the patent literature, such as in U.S. Pat. No. 5,451,233. Additionally, the various hubs 106, 112, 118 may include hemostasis valves which allow the shafts to move relative to one another while preventing blood or other fluids from exiting the proximal portion of the delivery catheter. A hemostasis valve such as a Tuohy-Borst may also be used to tighten down on a shaft to prevent the shaft from moving relative to another shaft. Therefore, the Tuohy-Borst may be used as a locking mechanism as well.

A stent 128 is disposed over the middle shaft 108 in a collapsed configuration sized for delivery. A pair of stops 130, 132 prevent the stent 128 from moving proximally or distally along the middle shaft 108 during delivery and deployment. The stops 130, 132 may be rings, bands, steps, bushings, sleeves, bumps, flanges, raised annular sections, or other structures which prevent the stent 128 from sliding along the middle shaft 108. The stops 130, 132 may be radiopaque to allow visualization of the proximal and distal ends of the stent under fluoroscopy during the stent procedure. Other visualization techniques may also be used such as x-ray, endoscopy, IVUS, MRI, ultrasound, and CT, as well as other techniques. Stent 128 is preferably a self expanding stent and therefore shuttle sheath 120 is disposed over the stent 128 in order to constrain it and prevent radial expansion thereof. The stent 128 may be fabricated from self expanding or shape memory alloys such as nitinol, spring steels, resilient polymer, or other materials known in the art. The shuttle sheath 120 is at least as long or longer than the length of the stent 128.

Outer shaft 114 also has a central lumen 116 extending between the proximal and distal ends of the shaft 114 so that the middle shaft 108 may be slidably disposed therein. A hub 118 on the proximal end of the outer shaft 114 provides the user a region for grasping, and also prevents the hub 112 on the middle shaft 108 from being advanced too far distally (or prevents the outer shaft 114 from being retracted proximally too far).

A proximal lock or coupling mechanism 122 couples the distal end of the outer shaft 113 with the proximal end of the shuttle sheath 120. A distal lock or coupling mechanism 124 couples distal end of the shuttle sheath 120 with the distal end of the inner shaft 102 via nosecone 126. The proximal and distal locks or coupling mechanisms may take a number of forms, including for example, snap fits, interference fits, barbed connectors, locking mechanisms, key locks, rotational or linear locks, threaded bushings, twist locks, magnetic couplings, bayonet coupling, breakable or frangible connectors, as well as others known in the art. The proximal coupling may take the same form as the distal coupling, or different couplings may be used on the proximal and distal ends. In this embodiment, the proximal lock 122 is locked (as indicated by the darkened rectangle 122), and the distal lock 124 is unlocked (as indicated by the white rectangle 124). This configuration allows preferential distal delivery of stent 128 as illustrated in FIGS. 1B-1D.

Figure 1B:
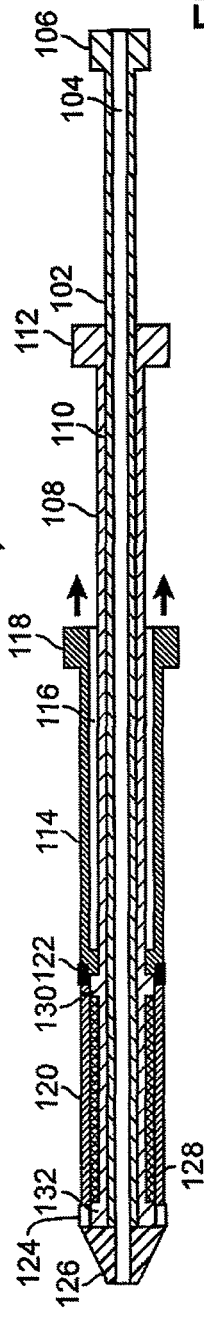
Figure 1C:
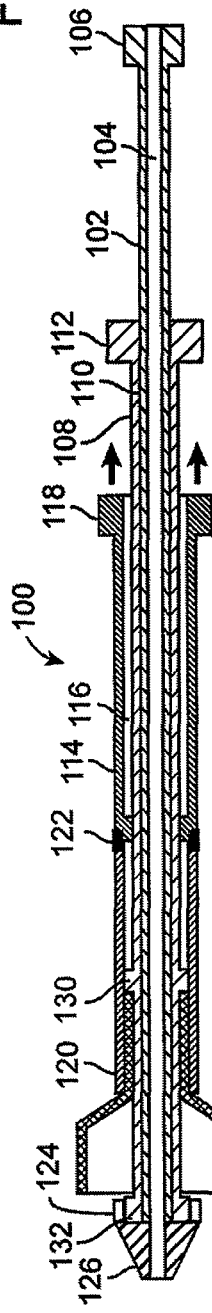
Figure 1D:
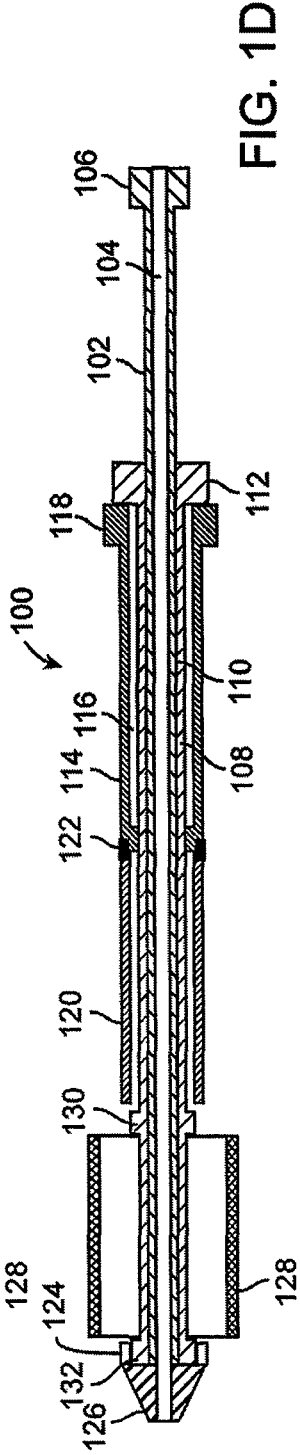

In FIG. 1B, the outer shaft 114 is retracted proximally relative to the middle shaft 108 and the inner shaft 102. Because outer shaft 114 is locked with shuttle sheath 120, and shuttle sheath 120 is unlocked from inner shaft 102, as the outer shaft 114 is proximally retracted, shuttle sheath 120 will also be proximally retracted. FIG. 1C shows that as shuttle sheath 120 is proximally retracted, stent 128 become partially unconstrained, allowing stent 128 to self expand into its radially expanded configuration. In this partially expanded configuration, a physician may optional re-advance the shuttle sheath 120 distally in order to draw the stent 128 back into a collapsed configuration constrained by shuttle sheath 120. This allows the stent to be repositioned if the initial deployment is not optimal. As shuttle sheath 120 continues to move proximally, stent 128 will also continue to self expand from its distal end toward its proximal end. FIG. 1D shows that once shuttle sheath 120 is fully retracted proximally and stent 128 is completely unconstrained, stent 128 fully expands into its radially expanded configuration. The delivery catheter 100 may then be retracted proximally through expanded stent 128 and removed from the patient. A handle (not illustrated) may be provided on the proximal end of the catheter with various actuation mechanisms (e.g. rotating knobs, sliding levers, etc.) to facilitate actuation of the shafts relative to one another. The handle may also be used with other embodiments disclosed herein. This delivery method may be used with a typical antegrade femoral vein approach. Distal release may also be used for stenting above the origin of the profunda when using a retrograde approach.

FIGS. 2A-2D illustrate the delivery system 100 configured preferentially for proximal delivery of a stent. FIG. 2A shows the delivery system 100 that is substantially the same as previously described above with respect to FIGS. 1A-1D, except the major difference being that the configuration of the proximal and distal locks or couplings 122, 124 has been reversed. In this exemplary embodiment, the distal lock 124 is now in a locked configuration such that shuttle sheath 120 is coupled with inner shaft 102 via nosecone 126. The locked configuration is indicated by the blackened rectangle 124. Proximal lock 122 is unlocked, therefore the shuttle sheath 120 is uncoupled from the outer shaft 114, as indicated by the white rectangle 122.

In FIG. 2B, the inner shaft 102 is advanced distally thereby also distally advancing shuttle sheath 120 relative to stent 128, as seen in FIG. 2C. As shuttle sheath 120 advanced distally, stent 128 becomes unconstrained, thereby allowing the unconstrained portion of stent 128 to self expand from its proximal end toward its distal end, into its radially expanded configuration. Additionally, when stent 128 is in a partially expanded configuration as shown in FIG. 2C, a physician optionally may proximally retract inner shaft 102 thereby retracting shuttle sheath 120 over stent 128 to recapture the stent and re-constrain the stent 128 in its collapsed configuration. This allows the physician to reposition the stent when its initial deployment is not optimal. FIG. 2D illustrates the stent 128 in its fully expanded configuration after shuttle sheath has been advanced distally so that stent 128 is unconstrained. The catheter 100 may then be retraced proximally through expanded stent 128 and removed from the patient. This method of delivery may be used during a contralateral retrograde venous approach or a jugular approach. Placement of the stent above the origin of the profunda vein is critical, therefore proximal release may also be used when using an antegrade approach.

In the examples illustrated in FIGS. 1A-1D and FIGS. 2A-2D, the proximal and distal locks or coupling mechanisms 122, 124 are pre-set to a locked or unlocked configuration. One of skill in the art will appreciate that any combination of locked and unlocked configurations is possible. Therefore the catheter may be supplied with both locks in the locked position, or both in the unlocked position. Also, the catheter may be supplied with proximal lock locked and the distal lock unlocked, or the catheter may be supplied with the proximal lock unlocked and the distal lock locked. The user may use the catheter as supplied, or the lock configuration may be changed by the user either prior to using the catheter, or in situ, depending on the desired stent deployment direction. Examples of various locking mechanisms application to this embodiment as well as the other embodiments disclosed herein are described in greater detail below.

FIGS. 3A-3E illustrate another exemplary embodiment of a bi-directional stent delivery system. The delivery system 300 may be used for either proximal or distal stent delivery depending on how the shafts are actuated. FIG. 3A illustrates the delivery system 300 prior to use in its preferred configuration. The system 300 includes an inner shaft 302, a middle shaft 308, an outer shaft 314, a shuttle sheath 320, and a stent 328. Each of the shafts 302, 308, 314 have a lumen extending between the proximal and distal ends of the shaft to allow the shafts to slidably receive one another and slidably move relative to one another. For example, inner shaft 302 is slidably disposed in the lumen of middle shaft 308, and middle shaft is slidably disposed in the lumen of outer shaft 314. Additionally, each shaft 302, 308, 314 also has a hub or flanged region 306, 312, 318 near the proximal end of the shaft and provides a region for an operator to grasp, as well as providing a stop to prevent the shafts from moving too far into one another. Other aspects of the hubs are generally similar to those previously described.

Stent 328 is constrained and held in a radially contracted configuration on the middle shaft 308 by shuttle sheath 320. Stent stops 330, 332 generally take the same form as those previously described above in FIGS. 1A-1D and 2A-2D. The stops 330, 332 prevent unwanted axial movement of stent 328 relative to middle shaft 308. A lock or coupling mechanism 324 couples the distal end of shuttle sheath 320 with the inner shaft 302 via nose cone 326. In this preferred embodiment, the lock is closed (as indicated by the darkened rectangle) so that shuttle sheath 320 is connected to inner shaft 302 via nose cone 326. The stent 328 generally takes the same form as stent 128 previously described above.

In FIG. 3B the inner shaft 302 is advanced distally. Because lock 324 is closed, shuttle sheath 320 will also move distally. As the shuttle sheath 320 is advanced distally, stent 328 will become unconstrained and will start to self-expand slightly until further expansion is constrained by outer shaft 314. As inner shaft 302 is further advanced distally, stent 328 becomes completely unconstrained and self expands into engagement with outer shaft 314 where further self expansion is prevented, as shown in FIG. 3C.

Outer shaft 314 may then be proximally retracted as illustrated in FIG. 3D. Proximal retraction of outer shaft 314 releases the constraint on stent 328 so that the stent may then self expand into its radially expanded configuration proximally. In FIG. 3D, the stent 328 is partially expanded and partially constrained. In this configuration, the operator may optionally re-advance the outer shaft 314 to recapture and reconstrain stent 328 into a collapsed configuration. This allows the stent 328 to be repositioned and redeployed if the initial position was not optimal. The outer shaft 314 is then fully retracted proximally so that stent 328 is fully unconstrained, and stent 328 radially expands into its fully expanded configuration. Catheter 300 may then be proximally retracted through the stent 328 and removed from the patient.

The lock 324 in FIGS. 3A-3E is preferably in the locked configuration so that proximal or distal movement of the inner shaft 302 will correspondingly move the shuttle sheath 320. One of skill in the art will appreciate that the catheter may be provided with the lock in the unlocked configuration, and the user may lock it as desired.

FIGS. 4A-4E illustrate how delivery catheter 300 in FIGS. 3A-3E may also be used for proximal stent deployment. The delivery system 300 in FIGS. 4A-4E is the same as the system described above in FIGS. 3A-3E, except that the order of shaft actuation is different, thereby allowing stent deployment in the opposite direction.

FIG. 4A shows the stent delivery system 300 prior to use. In FIG. 4B, the outer shaft 314 is proximally retracted until the shuttle sheath 320 is unconstrained by the outer shaft 314, as seen in FIG. 4C. In FIG. 4D, the inner shaft 302 is advanced distally. Because lock 324 is locked with shuttle sheath 320 via nose cone 326, the shuttle sheath 320 will also be advanced distally, thereby allowing stent 328 to self expand as the constraint provided by shuttle sheath 320 is removed. Also, as previously mentioned, while the stent is partially expanded, a physician may optionally recapture the stent and reposition it when the initial deployment is not optimal. The stent 328 may be recaptured by retracting the inner shaft 302, thereby also proximally retracting shuttle sheath 320 so that stent 328 returns to its collapsed configuration constrained by shuttle sheath 320. In FIG. 4E, the inner shaft is advanced distally so that shuttle sheath 320 is removed from stent 328. Stent 328 is then unconstrained and can radially expand fully into its expanded configuration. Delivery catheter 300 may then be retracted proximally through stent 328 and removed from the patient.

FIGS. 5A-5F illustrate another exemplary embodiment of a bi-directional stent delivery system 500. This embodiment is similar to that previously described above in FIGS. 1A-1D and FIGS. 2A-2D, with the major difference being that this embodiment delivers two stents, one preferably with proximal release and the other preferably with distal release. FIG. 5A shows stent delivery system 500 having an inner shaft 502, a middle shaft 508, an outer shaft 514, a shuttle sheath 520, and two stents 528, 529. All three shafts 502, 508, 514 have a central lumen extending between the proximal and distal ends of the shafts in order to allow the shafts to move relative to one another. Inner shaft 502 is slidably disposed in the lumen of middle shaft 508, and middle shaft 508 is slidably disposed in the lumen of outer shaft 514. Also, a hub or flanged region 506, 512, 518 on the proximal end of each shaft 502, 508, 514 provides a region for the physician to grasp during usage and actuation, as well as providing a stop to prevent excessive shaft movement. Moreover, in this embodiment, as well as the previous embodiments, the hubs may have standard fittings on them such as Luer tapers or threaded portions for coupling with a syringe, tube, or other device. Other features of the hubs previously described may also be employed in this embodiment.

Stents 528, 529 are disposed over middle shaft 508, and stent stops 530, 531, 532 prevent unwanted axial movement of the stents along the middle shaft 514. The stents 528, 529 and stent stops 530, 531, 532 generally take the same form as those previously described above. Locks or coupling mechanisms 522, 524 couple the shuttle sheath 520 with either the inner shaft 502 or the outer shaft 514 as will be described in greater detail below. In FIG. 5A, lock 524 is closed or locked (as indicated by the darkened rectangle) such that shuttle sheath 520 is connected to inner shaft 502 via nose cone 526. Lock 522 is unlocked (as indicated by the white rectangle) such that outer shaft 514 is free to move relative to shuttle sheath 520.

In FIG. 5B, inner shaft 502 is advanced distally, thereby correspondingly advancing shuttle sheath 520 distally. As the proximal most stent 529 becomes unconstrained, it partially self expands into its radially expanded configuration. At this point, the physician may optionally retract the inner shaft 502 to recapture and constrain the stent 529 into its radially collapsed configuration if repositioning is desired. Otherwise, the inner shaft 502 is advanced distally until stent 529 becomes fully unconstrained and it radially expands into its expanded configuration as illustrated in FIG. 5C. Inner shaft 502 may further be advanced distally to permit distal release the distal most stent 528, or as seen in FIG. 5D, the inner shaft is proximally retracted and the distal lock or connector 524 is unlocked (illustrated by the white rectangle) and the proximal lock or connector 522 is locked (illustrated by the darkened rectangle).

In FIG. 5E the outer shaft 514 is then retracted proximally, thereby also proximally retracting shuttle heath 520 so that stent 528 becomes unconstrained. This permits stent 528 to radially self expand. While the stent 528 is partially expanded and partially collapsed, the outer shaft 514 may optionally be advanced distally to recapture and reconstrain the stent 528 in the radially collapsed configuration in case repositioning is desired. Otherwise, as seen in FIG. 5F, the outer shaft 514 is further retracted proximally until stent 528 is no longer constrained, and it self-expands into the radially expanded configuration, in a proximal direction (opposite of the first stent 529). Delivery system 500 may then be retracted proximally through stents 528, 529 and removed from the patient.

In this embodiment, one of skill in the art will appreciate that any order of stent deployment may be used. For example, both stents may be deployed proximally, or both may be deployed distally. In still other embodiments, the proximal stent may be deployed proximally while the distal stent is deployed distally. In yet other embodiments the proximal stent may be deployed distally, and the distal stent may be deployed proximally. Deployment direction will depend on the order of actuation of the shafts and the coupling and uncoupling of the shuttle sheath with the inner and outer shafts. Furthermore, any number of stents may be carried by the delivery system, and the exemplary embodiment is not intended to limit the system to delivery of two stents.

Figure 10A:
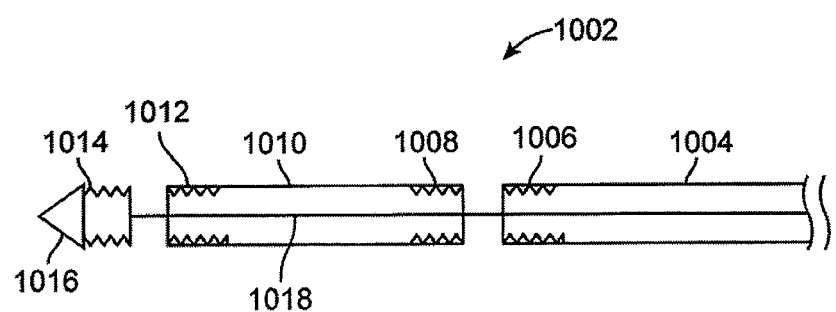
FIG. 10A-10E illustrates exemplary embodiments of threaded coupling mechanisms.

Any of the embodiments described above may have a number of different locking mechanisms or couplings that releasably join the shuttle sheath with the either the inner shaft or the outer shaft. For example, FIG. 10A illustrates how threaded couplings may be used. The delivery catheter 1002 includes an outer shaft 1004, inner shaft 1018, shuttle sheath 1010, and nose cone 1016 coupled to the inner shaft 1018. The middle shaft and stent described in embodiments above have been omitted for clarity. The outer shaft 1004 includes a threaded distal portion 1006 and the proximal portion of shuttle sheath 1010 also includes a threaded portion 1008. The distal portion of the shuttle sheath 1010 also includes a threaded portion 1012, and a proximal portion of nose cone 1016 includes a threaded portion 1014. The outer shaft 1004 may be rotated and advanced distally relative to the shuttle sheath 1010 thereby threadably engaging the outer shaft 1004 with the shuttle sheath 1010. Similarly, the inner shaft 1018 may be rotated and retracted proximally relative to the shuttle sheath, thereby threadably engaging the nose cone 1016 and inner shaft 1004 with the shuttle sheath 1010. The threads may be in same direction, or preferably are in different directions so that rotation in one direction couples the shuttle sheath with one of the shafts, and uncouples the shuttle sheath with the remaining shaft. Similarly rotation in the opposite direction uncouples the sheath from one shaft, and couples it with the remaining shaft. The threads often are either left handed or right handed. Additionally, in systems where the couplings are pre-set, the couplings may be uncoupled or coupled together. Male or female threads may be interchanged on the shuttle sheath and corresponding shaft.

Figure 10B:
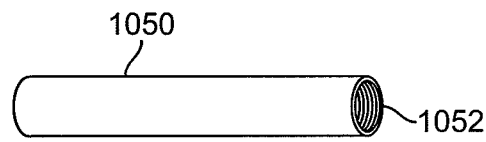
Figure 10C:
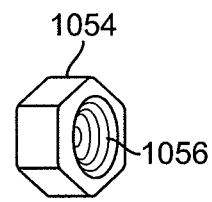
Figure 10D:
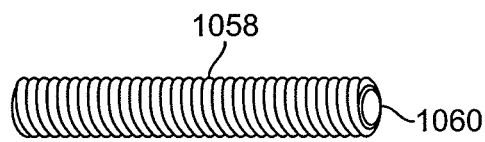
Figure 10E:
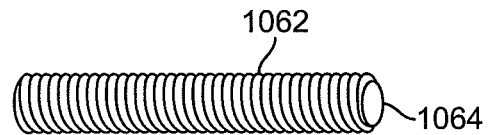

FIGS. 10B-10E illustrate exemplary embodiments of threaded couplings which may be used on either end of the shuttle sheath, the inner shaft, or outer shaft to create the coupling mechanism in any of the embodiments described herein. For example, FIG. 10B illustrates a threaded tube 1050 with internal threads 1052, and FIG. 10C illustrates a threaded nut 1054 also with internal threads 1056. Threaded rods such as in FIGS. 10D-10E may be threadably engaged with the embodiments of FIGS. 10B-10C. FIG. 10D illustrates a threaded rod 1058 having external threads and a central channel 1060 extending through the threaded rod. FIG. 10E illustrates another threaded rod 1062 having external threads, but having a solid center 1064.

Another exemplary embodiment of a coupling or locking mechanism 124, 122, 324, 524, 522, 612, 608, 712, and 708 is a bayonet coupling, sometimes also referred to as a screw-snap connector, or BNC connector. The coupling, connectors or locking mechanisms described herein may be used to releasably couple the shuttle sheath with either the inner shaft or the outer shaft, or both. The embodiments that follow may be used with any of the embodiments of delivery systems described herein. FIGS. 10F-10M illustrate various aspects of a number of alternative embodiments of this type of coupling, connecting of locking mechanism.

Figure 10F:
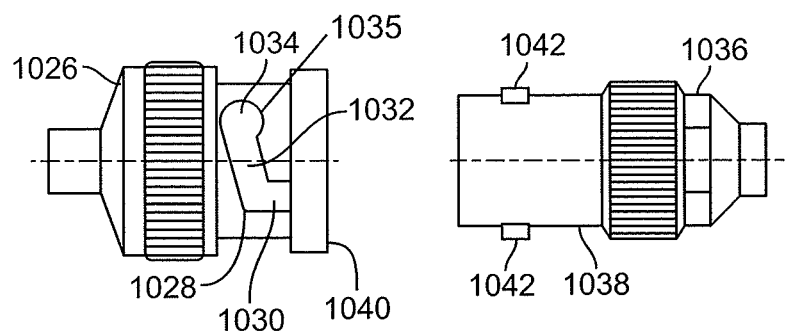
FIG. 10F illustrates an exemplary embodiment of a bayonet coupling mechanism.

Turning now to the coupling and locking mechanism illustrated in illustrated in FIG. 10F. In this embodiment, the connector or bayonet coupling includes a female connector 1026 and a male connector 1036. The female connector 1026 includes a central channel 1040 and at least one, and preferably two or more slotted channels 1028 that extend through a sidewall of the female connector 1026. The slotted channel 1028 has a linear portion or section 1030, a transverse portion or section 1032 and a receiver 1034. As further illustrated and described in the embodiments that follow, the relative length, size and orientation of the each of the sections 1030, 1032, 1034 of a coupler may vary depending upon a number of design factors.

In the illustrated embodiment of FIG. 10F, the linear portion or section 1030 is generally parallel to the longitudinal axis of the connector 1026. FIG. 10F also illustrates a transverse portion or section 1032 disposed at an angle relative to the linear portion or section 1030. In one aspect, the receiver section or portion 1034 has a diameter different from than another portion or section of the slot 1028. The diameter of the receiver may be larger or smaller than other diameters. As illustrated, the receiver 1034 includes a bulbous or flared end with a diameter larger than the other portions of slot 1028. In one aspect, the receiver section or portion 1034 has a shape different from another portion or section of the slot 1028. In the embodiment of FIG. 10F, the slot 1028 has a generally rectangular shape while the receiver 1030 has a circular shape.

FIG. 10F also illustrates a view of a male connector 1036. The male connector 1036 includes an elongate distal portion 1038 that may be received in the central channel 1040 of the female connector 1026. At least one, and preferably two or more pins 1042 extend radially outward from the elongate distal portion 1038. In use, the male connector 1036 is inserted into the female connector 1026 such that the elongate distal portion 1038 is received in the central channel 1040. The pins 1042 are aligned with the slot 1028, thus as the male connector is inserted into the female connector, the pin is advanced along the slot 1028 to the receiver section 1034. Relative movement between the male and female connectors results in the movement of a pin 1042 along the slot 1028. The degree and type of relative coupler movement will vary depending upon the shape and orientation of the various sections of the slot 1028.

Looking specifically at the slot in FIG. 10F, the pin 1042 is introduced into the linear section 1030 as the male distal portion 1038 enters the central channel 1040. Continued movement of the male connector into the female connector will advance the pin 1042 along the linear portion 1030 of the slot until it reaches the end of the linear portion. The male connector 1036 is then rotated relative to the female connector 1026 so that the pin 1042 then advances along the transverse portion 1032 of the slot until it reaches the end of transverse portion. As shown in FIG. 10F, the pin 1042 may rest in a receiver section 1034 having one or more features adapted to receive the pin 1042. The slot may also include one or more appropriately placed notches, indentations, detents, slits, or grooves to aid in maintaining one or more pins in a specific location along any of the sections of a slot. In the illustrated embodiment, the receiver 1034 includes a rounded out portion 1035 sized, shaped and configured to mate with the pin 1034. While the rounded portion 1035 and the pin 1034 employ complementary rounded surfaces to facilitate mating the pin into the receiver, a portion of a slot and a portion of a pin may be configured to have any of a number of complementary features to ensure the pin remains within a selected position or condition within the slot 1028. Furthermore, in some embodiments, a spring (not illustrated) is included in the bayonet coupling. The spring may be configured in the coupling to force the male connector away from the female connector. The spring force may be used to ensure that the pin 1042 then nests in receiver 1034. In addition or alternatively, the spring force may be used to maintain the pin 1042 within or in an engaged configuration with a suitable detent, notch, or locking feature located in a slot or within the female coupling. One example of such a suitable detent is the rounded portion 1035 in female coupling 1026. Any of the above mentioned or other suitable mating locking features may be employed for locking the male and female connectors together.

In the locked configuration, the two connectors 1026, 1036 are engages with the male connector inside of the central channel 1040 with the pin 1042 in the receiver rounded portion 1035. The two connectors 1026, 1036 may be released from one another by appropriate movements depending upon the specific coupler connection used such the slot configuration or specifics of a particular locking feature, if used. The pin 1042 may be seated along the slot 1028 by a friction fit. A friction fit may be introduced along the slot by, for example, reducing the diameter of the slot relative to the diameter or size of one or more pins so when the pin or pins move into a reduced size or diameter section of the slot, the pin is wedged into that position.

In the embodiment illustrated in FIG. 10F, first pressing the male connector inward relative to the female connector will move the pin 1042 out of engagement with the rounded receiver portion 1035. Next, by rotating the two connectors 1026, 1036 relative to one another, the pin 1042 will slide along the transverse portion and translate so that the pin slides outward along the transverse portion. Next, as the two connectors 1026, 1036 are pulled apart relative to one another, the pin 1042 is moved along and then released from the linear portion 1030 of the slot. Either the male or female connector may be used on one end of the shuttle sheath 120, 320, 520, 610 or 719, with the opposite connector used on the inner or outer shaft to which the shuttle sheath is releasably connected. Additionally, just as threads have "handedness," the bayonet coupling may also have left-handed and right-handed mechanisms such that rotation in one direction releases the connector, while rotation in the opposite direction couples the connector. Thus a left handed bayonet coupling may be used on one end of the shuttle sheath, while a right handed bayonet coupling may be used on the opposite end of the shuttle sheath. This allows one end of the shuttle sheath to be connected without connecting the opposite end. The operation of the locking or coupling mechanisms is further described below with reference to FIGS. 14A-15D.

Figure 10G:
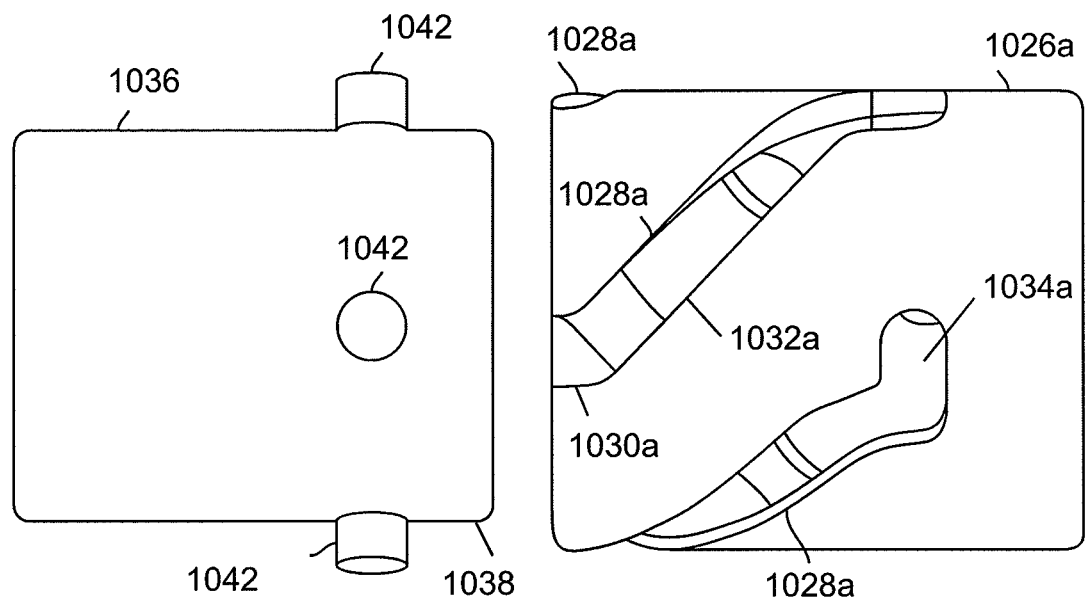
FIGS. 10G-10M illustrate other exemplary embodiments of a bayonet coupling mechanism.
Figure 10H:
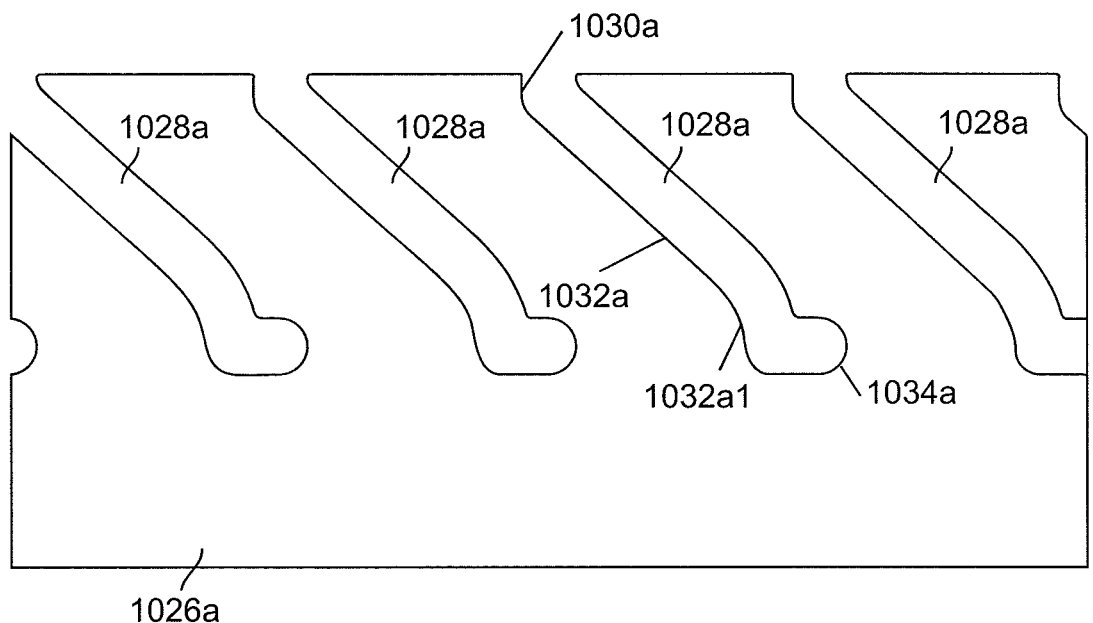

FIGS. 10G-10H illustrate another exemplary embodiment of a bayonet coupling. This embodiment is similar to the previous bayonet coupling in FIG. 10F, but instead of having two pins 1042 that mate with two slots 1028, this embodiment has four pins 1042 that mate with four slots 1028*a*. FIG. 10G illustrates the male connector 1036 that is generally cylindrical and having four pins 1042 that extend radially outward from the body of the connector distal portion 1038. The pins 1042 are preferably spaced 90 degrees apart, but this is not intended to be limiting. The female connector 1026*a* includes four slots 1028*a*, preferably spaced 90 degrees apart. The slots 1026*a* include a lateral section 1030*a*, a transverse section 1032*a* and a receiver section 1034*a*. The transverse section 1032*a* also includes an additional curved portion 1032*a*1 as a transition between the transverse section and the receiver section. The slots 1028*a* are sized to receive the pins 1042 when the male connector distal portion 1038 is inserted into the female connector and then moved, advanced or rotated relative to one another as needed to advance pins 1042 along the slots 1028*a*. The lateral portion 1030*a* is shorter than that of the embodiment of FIG. 10F. The receiver section 1034*a* does not have a rounded section 1035 as in the embodiment of FIG. 10F. Other aspects of the male and female connector, and their operation generally take the same form as describe with respect to FIG. 10F above.

FIG. 10H illustrates an exemplary method of forming the slotted female connector from a flat sheet. The slots 1028*a* may be machined (e.g. by EDM, photochemically etched, laser cut, etc.) into a flat sheet of material that is then rolled into a cylindrical shape to form the female connector 1026*a* as seen in FIG. 10G. As in any of the embodiments described herein, the female connector may also be cut from a tube. The male connector may be formed by press fitting, bonding, welding, etc. pins into the male connector or machined or molded.

Figure 10I:
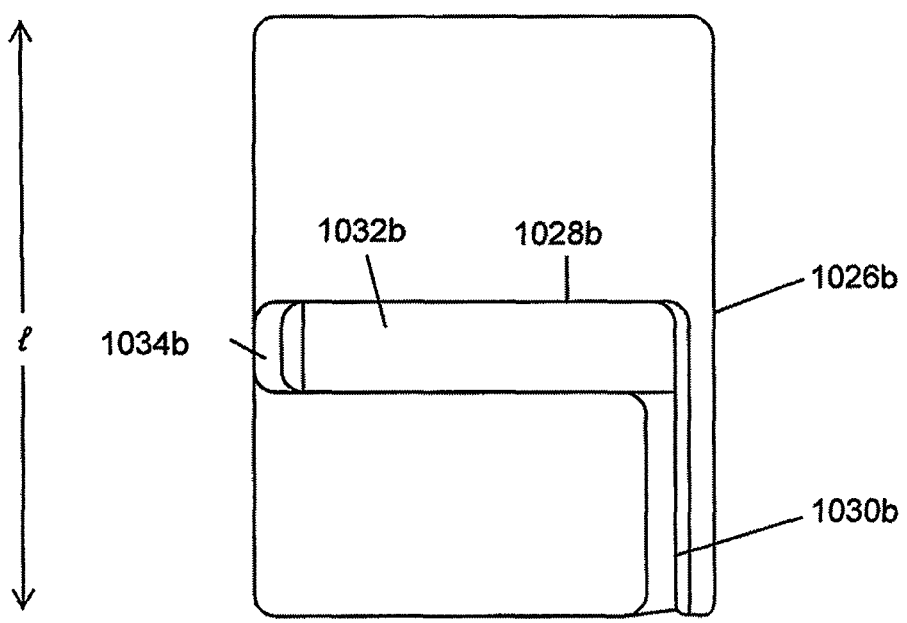
Figure 10J:
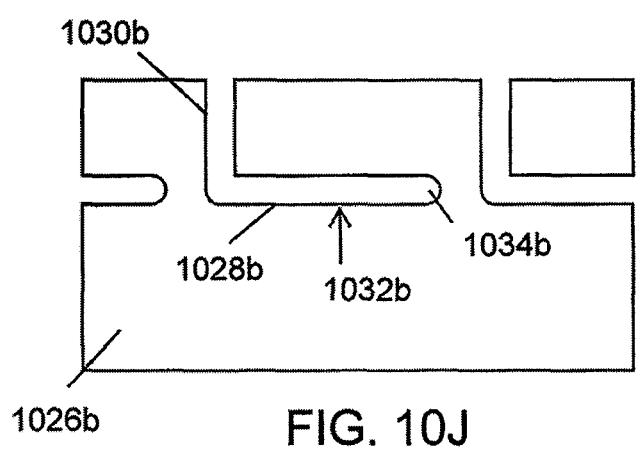

FIGS. 10I-10M illustrate additional, exemplary embodiments of the bayonet couplings illustrated in FIGS. 10F and 10G. FIGS. 10I and 10J illustrate views of a female coupler 1026*b* similar to the previous female bayonet couplings shown in FIGS. 10F and 10G that is that FIG. 10I is an overall perspective view while FIG. 10J illustrates the coupler as a flat sheet. The coupling 1026*b* includes slots 1028*b* having a linear section 1030*b*, a transverse section 1032*b* and a receiver section 1034*b*. In this illustrative embodiment, the longitudinal section 1030*b* and the transverse section 1032 bare preferably oriented at an angle that is 90 degrees. The female connector 1026*b* is designed to mate with a two pin male connector 1036 similar to the previous bayonet coupling in FIG. 10F. Other aspects of the male and female connectors, and their operation generally take the same form as described with respect to male and female connectors 1026, 1036 in FIGS. 10F and 10G.

Figure 10M:
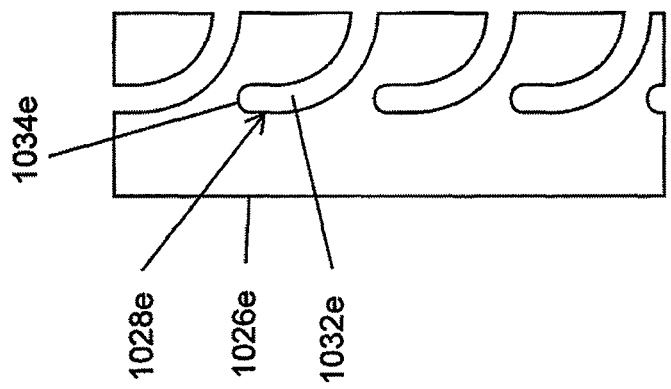
Figure 10K:
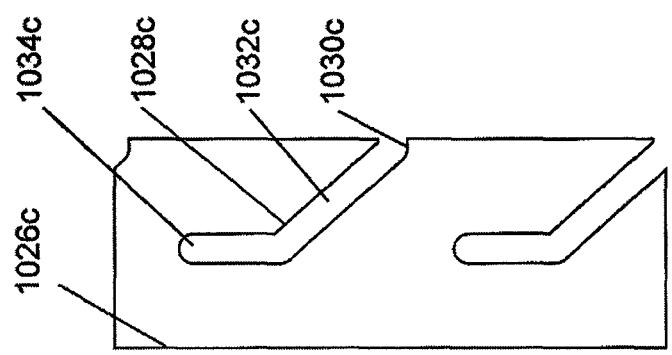
Figure 10L:
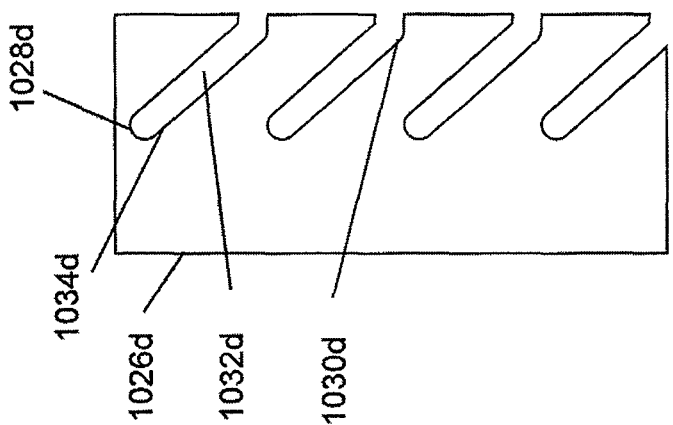

FIGS. 10K, 10L and 10M illustrate additional slot design alternatives. For simplicity of comparison, these alternative slot designs are shown on a flat sheet as in FIGS. 10H and 10J and can similarly be rolled or otherwise formed into a female connector as discussed above.

FIG. 10K illustrates an alternative slot 1028*c* as part of the female coupling 1026*c*. The slot 1028*c* includes a linear section 1030*c*, a transverse section 1032*c* and a receiver section 1034*c*. As with the receiver section in FIG. 10J, the receiver 1034*c* also extends along the circumference of the female connector in an orientation generally orthogonal to the longitudinal axis of the connector. The linear 1030*c* and transverse 1032*c* sections in FIG. 10K are arranged at an angle of about 45 degrees in contrast to the 90 degree relationship shown in FIG. 10J.

Another alternative slot 1028*d* configuration is illustrated in the female coupling 1026*d* in FIG. 10L. The linear 1030*d* and transverse 1032*d* sections in FIG. 10L are arranged at an angle of about 45 degrees just as in FIG. 10K. The slot 1028*d* in FIG. 10L does not have an elongated receiver section, in contrast to FIGS. 10K, and 10F. The receiver section 1034*d* in FIG. 10L has the same diameter as the transverse section 1032*d* as in FIG. 10K and in contrast to the enlarged diameter receiver section 1034 shown in FIG. 10F (i.e., rounded portion 1035).

Another alternative slot configuration is shown in the female coupling 1026*e* illustrated in FIG. 10M. In contrast to the discrete linear and transverse sections of the slot in FIG. 10J, the slot 1028*e* in FIG. 10M is only a transverse section 1032*e*. In the illustrated embodiment, the transverse section 1032*e* sweeps out a curve of about 90 degrees. As with prior embodiments, the receiver section 1034*e* has the same dimensions as the transverse section 1032*e*. The transverse section 1032*e* may include other shapes as well including compound curves such as those illustrated in FIG. 10H, for example at 1032*a*1.

As is clear from the discussion above, there are numerous slotted channel embodiments are possible. There are also several exemplary methods of forming the slotted female coupling from a flat sheet. In general, the configuration and size of the slots in a female connector may vary and include one or more of a transverse section, a longitudinal section, an angled section, a curvilinear section, a receiver (end) section, or combinations thereof. The pins of the male connector are sized and spaced in accordance with the corresponding female connector. The length, width and relative proportion of the various slot sections may vary depending upon various design considerations. In one exemplary embodiment, the female connector can have an overall length of 0.050-1.000", with a preferred length of 0.100-0.500". The slot of the female coupling can have a width of 0.010-0.050", preferably 0.015-0.030" and a length of 0.050-1.500", preferably 0.100-0.500". (see FIG. 10I for an indication of overall length "1" of the female coupler). The slot of the female coupling can define a path of travel for a pin of from 0.1 to about 3 rotations, preferably 0.25-1 rotations, around the circumference of the coupling. The number of slots in the female connector can be 1 or more, 2 slots, 3 slots or 4 slots. The female connector slot can have transverse and longitudinal sections arranged in angles at 90 degrees (FIG. 10J), 45 degrees (FIG. 10L) or anywhere in a range from 60-150 degrees, preferably in a range 80-100 degrees. The receiver section 1034 can have an flared section of larger diameter than an adjacent section, an enlarged, rounded section (see receiver 1034 in FIG. 10F), an elongated receiver section (a longer version is shown in FIG. 10K and a shorter versions are shown in FIGS. 10G and 10H) with a diameter similar to an adjacent slot section. In another alternative, the receiver section at the end of the slot that can be narrower than one or more of the other slot sections. In one aspect, the receiver section has a narrower width than one or more slot sections having a width that ranges from about 0.005-0.020" as compared to the width of other slot sections.

Like FIG. 10H, FIGS. 10J, 10K, 10L and 10M, each illustrate an exemplary method of forming the slotted female connectors shown in FIGS. 10F, 10G and 10I from a flat sheet. The slots may be machined (e.g. by EDM, photochemically etched, laser cut, etc.) into a flat sheet of material that is then rolled into a cylindrical shape to form the female connector. As with all female connector embodiments described herein, the connector may also be cut from a tube. As with all the male connector embodiments, the male connector may be formed by press fitting, bonding, welding, etc. pins 1042, 1078 into the male connector. Alternatively, the pins may be machined or molded. The pins are spaced, sized and shaped to mate with the corresponding female connector as described herein.

Figure 11A:
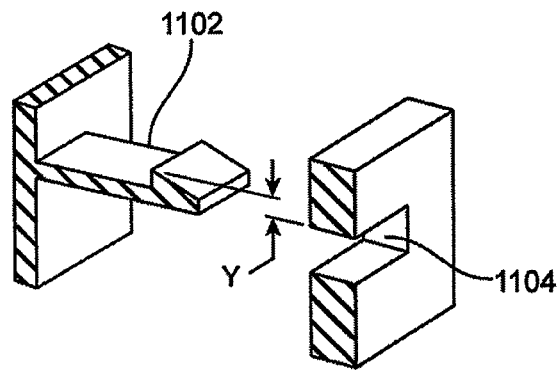
FIGS. 11A-11C illustrate exemplary embodiments of snap fits.
Figure 11B:
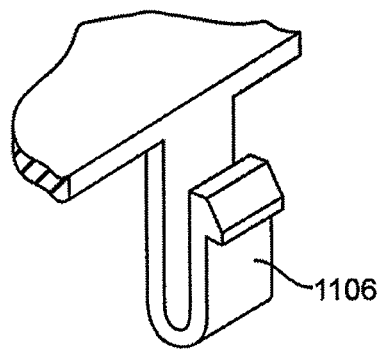
Figure 11C:
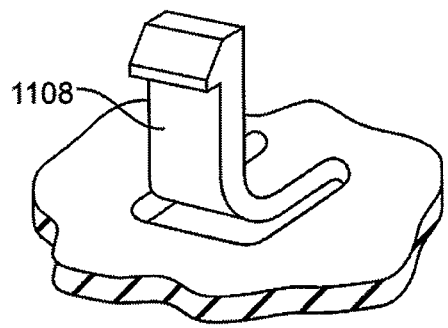

Other connectors include frangible connectors fabricated from breakable wires, strands, fibers, tubes, tabs, hooks, barbs, cantilevers, etc. that remain intact and connected until a certain force is applied, and the connector breaks. While these connectors are promising, they only allow the connection to be broken a single time, and reconnection is not possible. Therefore preferred embodiments may be connected and unconnected multiple times. FIGS. 11A-11C also illustrate snap fits which may be used as the connector mechanism. FIG. 11A illustrates a cantilevered snap fitting 1102 that locks with a recessed region 1104 in the mating part. FIG. 1106 illustrates a "U" shaped cantilevered snap fit 1106, and FIG. 11C illustrates an "L" shaped cantilevered snap fitting 1108. The cantilevered snap fitting may be a part of the shuttle sheath that mates with the recessed portion on one of the shafts, or the snap fitting may be on the shafts and the recessed portion may be a part of the shuttle sheath.

Figure 11D:
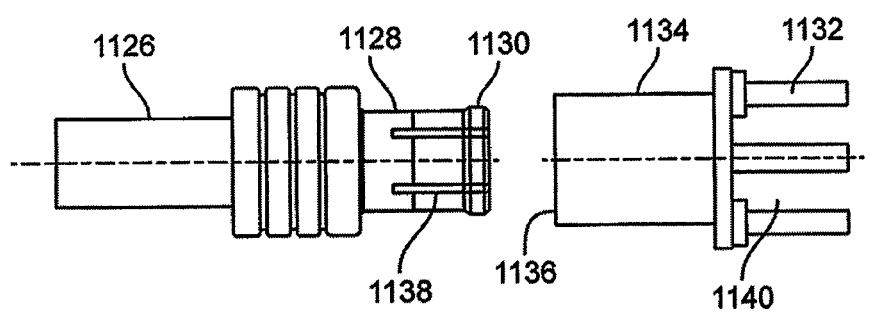
FIGS. 11D-11E illustrate still other embodiments of snap or press fit mechanisms.

FIG. 11D illustrates yet another embodiment of a snap fit that may be used to form the connector mechanisms described above. A connector includes a male portion 1126 and a female portion 1132. The male portion 1126 of the connector includes an elongate distal section 1128 having a raised annular flange 1130 near its distal end. A plurality of longitudinal slits 1138 form several resilient arms in the distal section 1128 that radially expand and contract. The female connector 1132 includes a proximal portion 1134 having a central channel 1136 therethrough. The central channel 1136 opens up into an enlarged region 1140. In use, the distal section 1128 is slidably inserted into the central channel 1136 forcing the resilient arms into a collapsed configuration. The male connector is advanced into the female connector until the annular flange 1130 enters the enlarged region 1140. The arms resiliently open back up to their unbiased configuration, forcing the annular flange outward, thereby releasably locking the male and female connectors together. The two may be pulled apart from one another upon application of adequate tensile force.

Figure 11E:
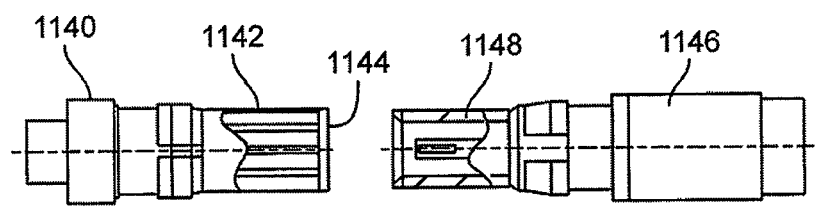

FIG. 11E illustrates a slide-on coupling mechanism which includes a male connector 1146 and a female connector 1140. The male connector has an elongate distal region 1148, and the female connector has a receiving portion 1142 with a central channel 1144 therethrough. The male and female connectors are pressed against one another such that the distal region 1148 is received in the receiving portion 1142. The size of the two connectors may be adjusted to provide an appropriate friction fit against one another to prevent unwanted release. The two connectors may be released from one another upon application of adequate tensile force.

Figure 12:
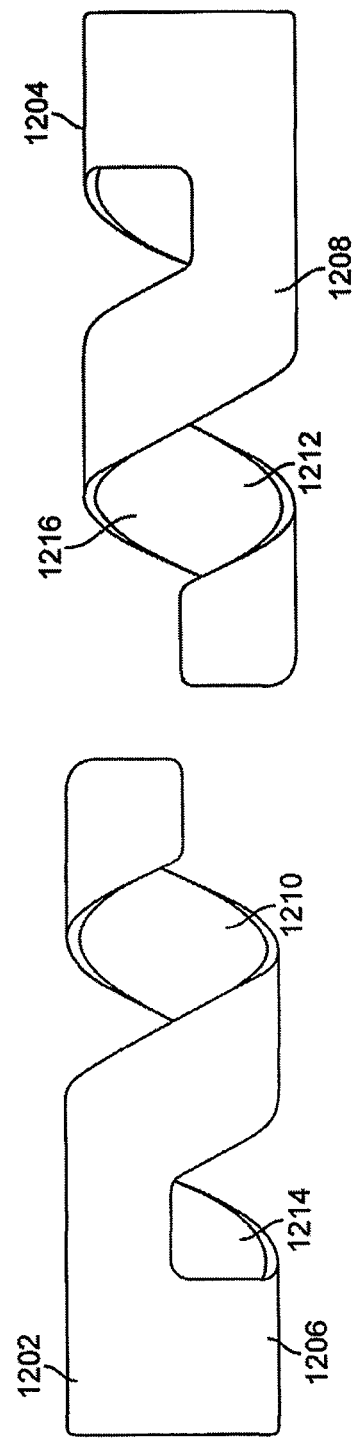
FIG. 12 illustrates yet another exemplary embodiment of a coupling mechanism.

FIG. 12 illustrates an exemplary embodiment of a spiral or helical coupling mechanism that may be used in any of the delivery catheter embodiments disclosed herein. The coupling mechanism includes a first spiral or helical connector 1202 and a second spiral or helical connector 1204. The first spiral connector includes a proximal portion 1206 that is preferably cylindrical and this may be joined by bonding, welding, threading, press fitting, etc. to either end of the shuttle sheath, or the inner shaft or outer shaft. A distal portion 1210 of the spiral connector winds in a spiral or helical pattern in a first direction to form a thread-like region. The outer diameter of the spiral connector is preferably constant along the entire length of the connector, but this is not intended to be limiting. Additionally, a central channel 1214 extends through spiral connector 1202, and the inner diameter of the first connector 1202 is also preferably constant along the connector, but not required. The second spiral connector 1204 is identical to the first connector 1202, rotated 180 degrees. The second connector 1204 includes a proximal portion 1208 that is also preferably cylindrical for joining with the shuttle sheath, inner shaft, or outer shaft by one of the methods listed above, or known to those of skill in the art. A distal portion 1208 of the second connector 1204 winds in a spiral or helical pattern in a second direction opposite the first direction to form a thread-like region. The outer diameter of the spiral connector 1204 is preferably constant along its entire length, but this is not meant to be limiting. Also, a central channel 1212 extends through the spiral connector 1204, and the inner diameter of second connector 1204 is also preferably constant along its length, but not required. The two connectors may be joined together by rotating one connector relative to the other connector so that the thread-like regions overlap and engage with one another. Also, similar to other threaded-type embodiments disclosed herein, when two spiral connectors are used on opposite ends of the shuttle sheath, rotation in one direction will couple the shuttle sheath to one of the shafts (inner or outer shaft) while decoupling the shuttle sheath from the other shaft. Similarly, rotation in the opposite direction will decouple the shuttle sheath at one end and couple it at the opposite end. The pitch of the helix is preferably set so that rotation is smooth with relatively low friction and so that the number of turns required to lock the two connectors together is comfortable to most operators. One advantage of this design is that both connectors may be cut from a single piece of tubing having a length less than the combined length of the individual connectors. Additionally, only a single connector need be manufactured since both halves are mirror images of one another. One connector may be used on one end of the shuttle sheath or shaft, while the same part may be flipped over and used on the opposite end. This is desirable since it helps reduce component inventory and ensures ease of manufacturing.

Figure 13:
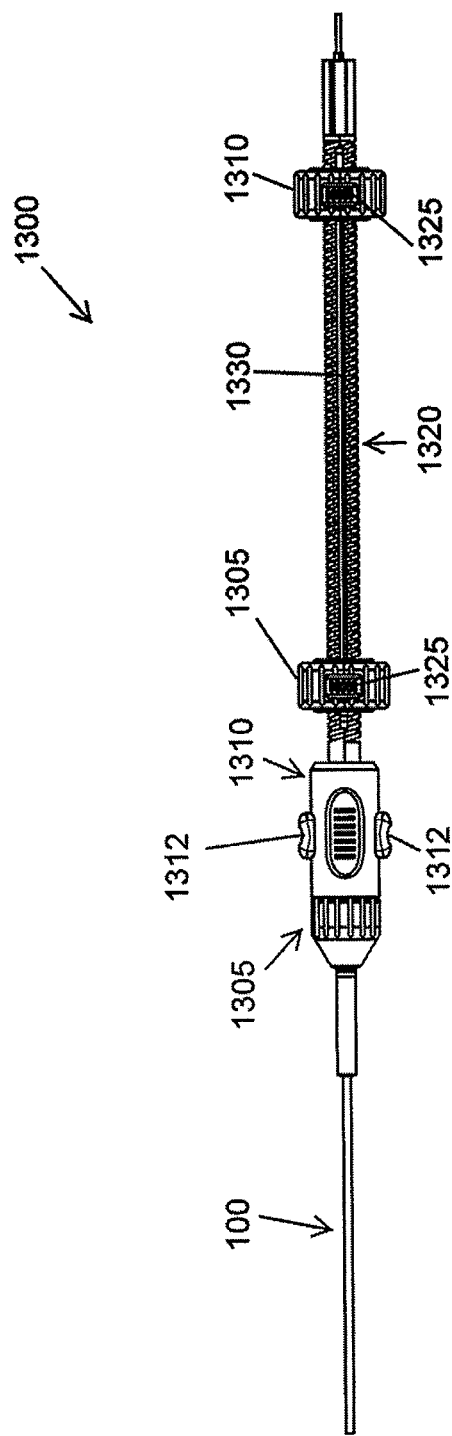
FIG. 13 illustrates an exemplary handle used to operate a bi-directional stent delivery catheter.

One embodiment of a bi-directional stent deployment handle 1300 is illustrated in FIG. 13. The operation of the handle to deploy a stent will be described in greater detail with regard to FIGS. 14A-15F. The handle 1300 is designed to work in conjunction with the sliding sheath based catheters 100, 300, 500, described herein that employ one or more severable connector or couplings. The connectors or couplings are placed in relation to the catheter components to capture and control the deployment of a stent. As discussed above, the connectors or couplings are placed proximal and distal to a stent section, thus allowing either end of the outer sheath or shuttle sheath to be disconnected and moved proximally or distally relative to the stent. This configuration advantageously allows the stent to be deployed in the traditional proximal to distal configuration or vice versa depending upon the deployment circumstances. Catheter connections to the handle allow the shuttle sheath or shafts to be remotely rotated and translated relative to each other to facilitate stent placement, deployment, capture or retrieval.

In one embodiment, the handle 1300 includes a de-coupling torque 1305, a selector switch, a proximal slider 1310 and a distal slider 1305. The de-coupling torque 1305 is connected to the outer sheath or shaft by a coupling mechanism as described herein (e.g., FIGS. 1A, 2a). Rotation of the de-coupling torquer 1305 allows the outer sheath or shaft to be rotated. The direction of rotation as either clockwise or counter-clockwise is determined by the position of the decoupling selector switch 1310. The distal/proximal decoupling selector switch 1310 or decoupling selector switch determines the direction in which the de-coupling torquer 1305 is allowed to rotate. As described herein, relative movement such as rotation between the shuttle sheath or one or more shafts may be used in some embodiments to engage or disengage a coupling or locking mechanism. In one aspect, the selector switch is used to determine the direction of rotation of the outer shaft relative to the inner members of the catheter, such as one or more shafts. In one aspect, the proximal sheath connector (i.e., the proximal end of a male/female connector) employs a right hand thread while the distal connector (i.e, the complementing male/female connector) relies on a left hand thread. As such, imparting rotation of the outer shaft with the torquer 1305 relative to the handle in one direction serves to loosen one connector while leaving the other intact. As a result, cooperation of the selector switch 1310 and torquer 1305 provides for distal or proximal release of a coupling mechanism depending on which direction the outer sheath is allowed to turn.

The selector switch 1310 restricts the rotational direction of the de-coupling torquer 1305 based on which direction is selected. In one aspect, moving the selector switch 1310 into a distal position allows the torquer 1305 to be rotated clockwise while restricting rotation in the counter clockwise direction. Alternatively, moving the selector switch 1310 into a proximal position has the opposite effect.

Like the torque 1305, the proximal and distal sliders are coupled to one or more shafts or sheaths or portions of the system 100 to permit relative movement and control of the catheter components. When used in the vasculature or lumens of a mammal, the handle 1300 will be outside of the body while the stent and other elements at the distal end of the catheter are located and are to be remotely actuated in the mammal (see, e.g., FIGS. 6A to 7C). The distal slider 1305 is connected to the outer sheath or shaft such that translation of the distal slider 1305 from distal to proximal produces the same movement of the outer shaft and structures attached to it such as the shuttle sheath. In this way, movement of the distal slider 1305 moves the outer shaft 114 to reveal the stent 128 in the same manner shown in FIG. 1C and elsewhere. It is to be appreciated that movement of the distal slider 1305 is akin to moving the outer shaft hub 118, 318 or 518 as described herein.

In one aspect, the distal slider 1305 has two modes of operation. The first mode allows fine movements of the outer shaft. Fine movement control may be provided in a number of ways. In one aspect, fine movements may be achieved by rotation of a slider 1305 on a threaded body of the handle 1305. The threaded portion 1320 shown in the illustrative embodiment of FIG. 13 is for such a purpose. An appropriate internal mechanism within the slider 1305 allows pure translation of the outer shaft by rotation of the slider control. In one specific embodiment, the pitch of threaded portion 1320 is such that one rotation of a slider 1305 translates the outer shaft approximately one (1) millimeter. Other thread pitches are possible to provide movements of less than 1 mm such as 0.5 mm or more than 1 mm such as 2, 3, 4, 5 or more millimeters per rotation of slider 1305. A second mode of operation of a slider 1305 allows for coarser/rapid movements of the outer sheath. In one aspect, this mode of slider operation is achieved by depressing a release button 1325 located on the slider. Depressing the release button 1325 on the slider control will decouple the slider mechanism from the threaded body of the handle. Once decoupled from threads 1320, the slider 1305 is free to move along slot 1330. Translating the slider along slot 1330 in the appropriate direction yields a corresponding equivalent movement or 1:1 movement of the outer shaft or components like the stent that are connected to it.

Regardless of the mode of operation, distal to proximal deployment of a stent is achieved by moving the distal control 1305 in the proximal direction along the handle. After deployment, the distal end of the catheter may be resheathed by moving the distal control 1305 back to the starting position.

The proximal slider 1310 is connected to the inner sheath or shaft such that translation of the proximal slider 1310 produces the same movement of the inner shaft and structures attached to it such as the shuttle sheath 120 or nose cone 126, for example as shown in FIGS. 2A-2D. In this way, the proximal slider 1310 may move or hold stationary the inner shaft 102 and related components to reveal the stent 128 in the same manner shown in FIG. 2C and elsewhere where inner shaft movement is used for deployment. It is to be appreciated that movement of the proximal slider 1310 is akin to moving the inner shaft hub 106, 306, or 506 as described herein.

In one aspect, the proximal slider control 1310 has fine and coarse control modes similar to those described above with the distal slider 1305. The proximal controller 1310 differs in one aspect in that stent deployment is achieved by moving the proximal slider 1310 in a distal direction. If needed, stent resheathing may be achieved by moving the proximal slider 1310 control back to the starting position.

By way of reviewing the handle design, one may consider that the basic design of the catheter is such that the proximal end terminates with three concentric tubes or shafts. The three tubes or shafts are the outer shaft, the midshaft and the inner shaft. Numerous alternatives embodiments of the relationship of the shafts and catheter components are shown and described above in FIGS. 1A-5F and connected to exemplary handle components in FIGS. 14A-15F.

In one specific embodiment, the deployment of a stent is produced when the tubes or shafts are manipulated in the following manner:

Distal to proximal deployment:
Outer shaft:
Rotate clockwise (when viewed from the distal end of the device) to decouple the distal coupler
Translate shaft proximal to reveal the stent
Translate shaft distal to resheath the distal end
Mid shaft:
Fixed relative to the handle
Inner shaft:
Fixed relative to the handle
Proximal to distal deployment:
Outer shaft:
Rotate counter-clockwise (when viewed from the distal end of the device) to decouple the proximal coupler
Shaft remains stationary with respect to translation after the above step
Mid shaft:
Fixed relative to the handle
Inner shaft:
Translate the shaft distal to reveal the stent
Translate the shaft proximal to resheath the distal end In one aspect, there are three basic independent motions of the shafts used in combination to achieve the above deployments:
1. Rotation in clockwise or counter clockwise direction of the outer shaft
2. Linear translation of the outer shaft
3. Linear translation of the inner shaft FIGS. 14A-14F illustrate a distal release stent deployment of the bi-directional delivery system. For simplicity, the deployment sequence and use of the handle 1300 will follow a sequence similar to the system deployment described in FIGS. 1A-1D. Additional details in this sequence are used to describe the decoupling of a coupling mechanism with the distal connectors starting from a pre-connected, locked or engaged state. A selector switch 1310, knob 1312 and a torquer 1305 are illustrated in each of the figures. The elements of the handle 1300 will be described to activate the delivery system for distal release and decouple the distal connectors, respectively. The female connector is an embodiment of the connector 1026b of FIG. 10I and those reference numbers apply. FIG. 14 A includes two enlarged portions 1 and 2 of the areas surrounding the connecting mechanisms 124, 122, respectively. The enlarged portions 1, 2 allow the workings of the connector to be seen relative to the various movements of the handle components.

Figure 14A:
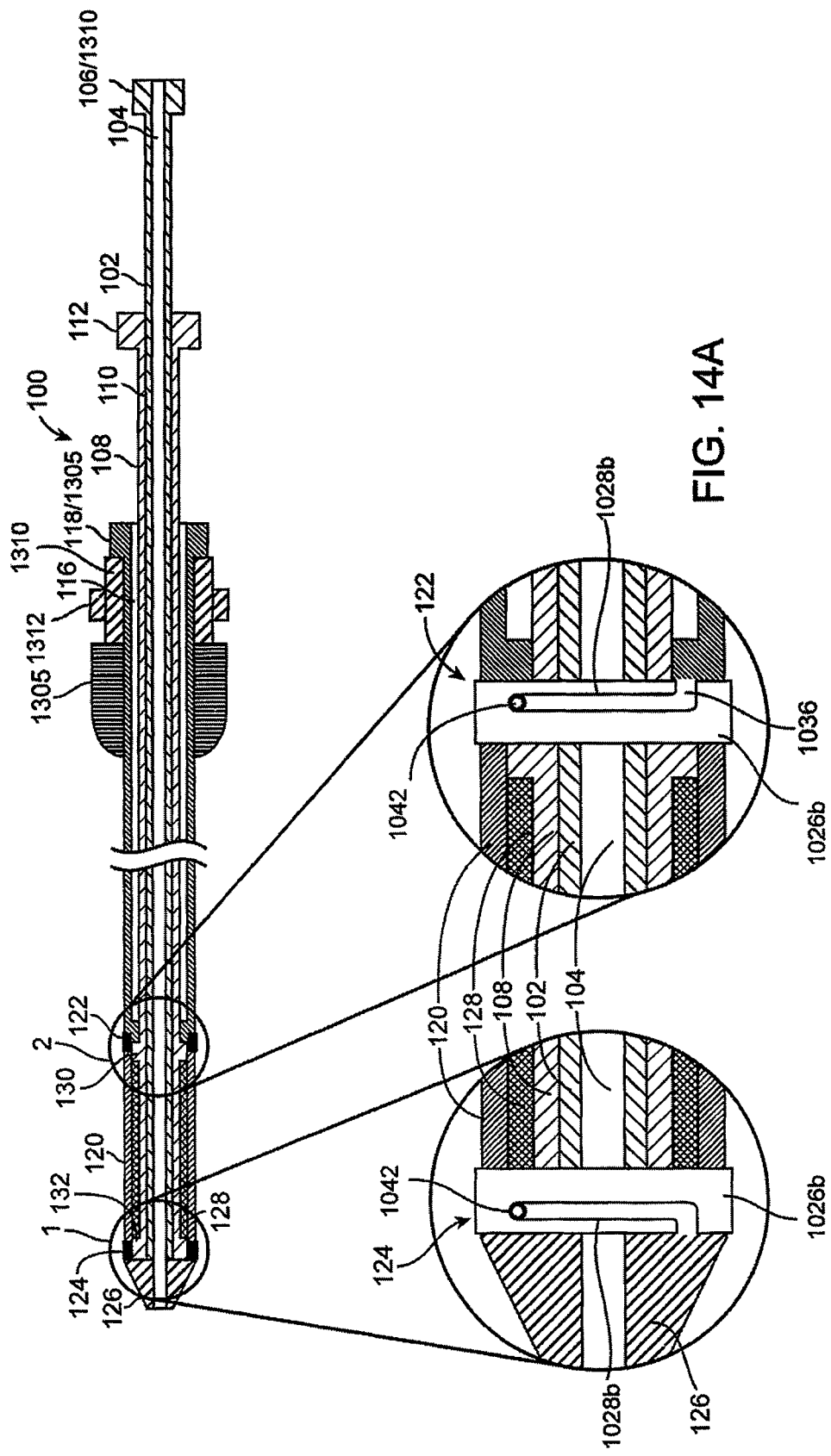
FIGS. 14A-14F illustrate an exemplary embodiment of a bi-directional stent delivery catheter configured for and demonstrating a distal stent release though use of the elements of a handle similar to that of FIG. 13.
Figure 14B:
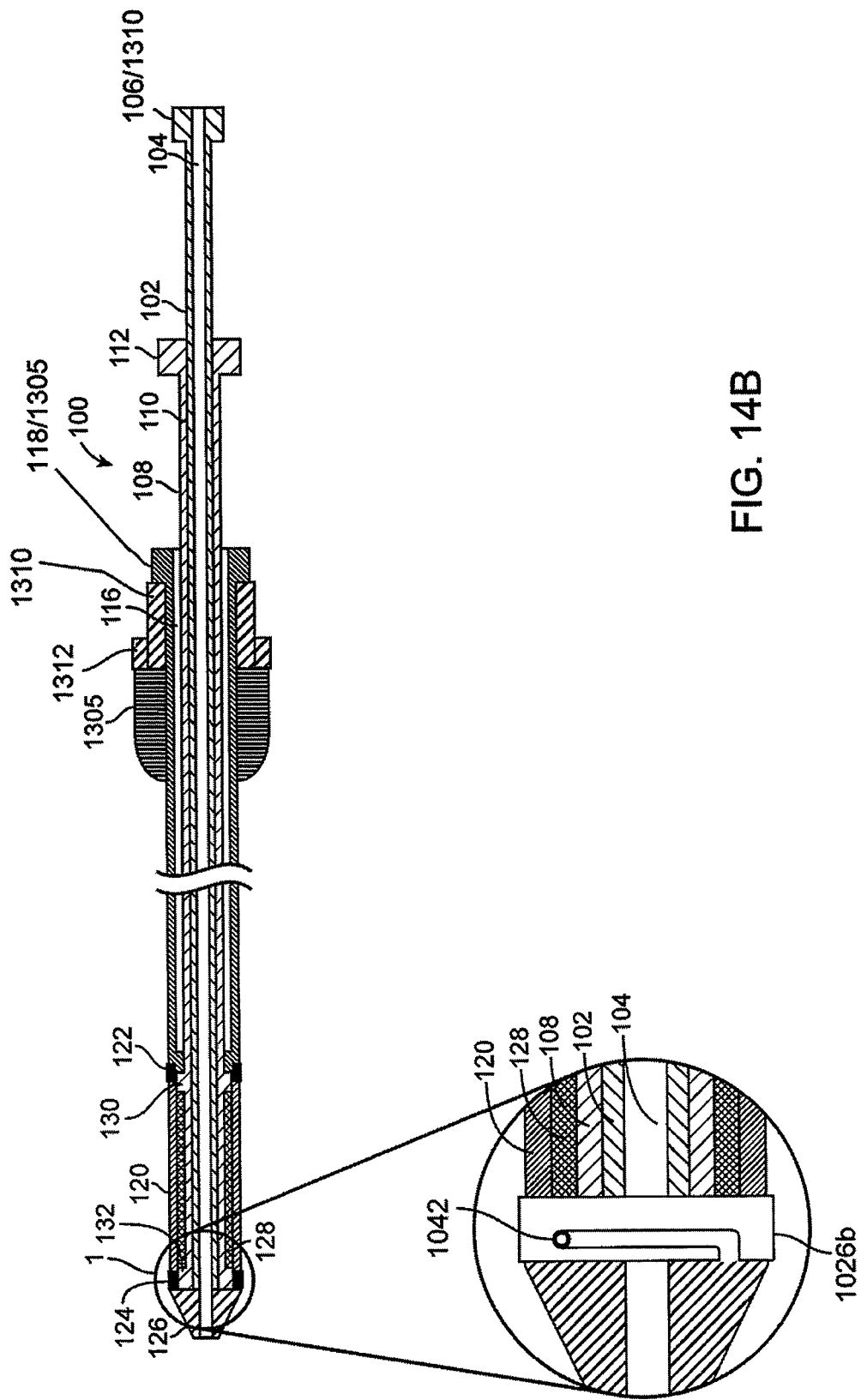
Figure 14C:
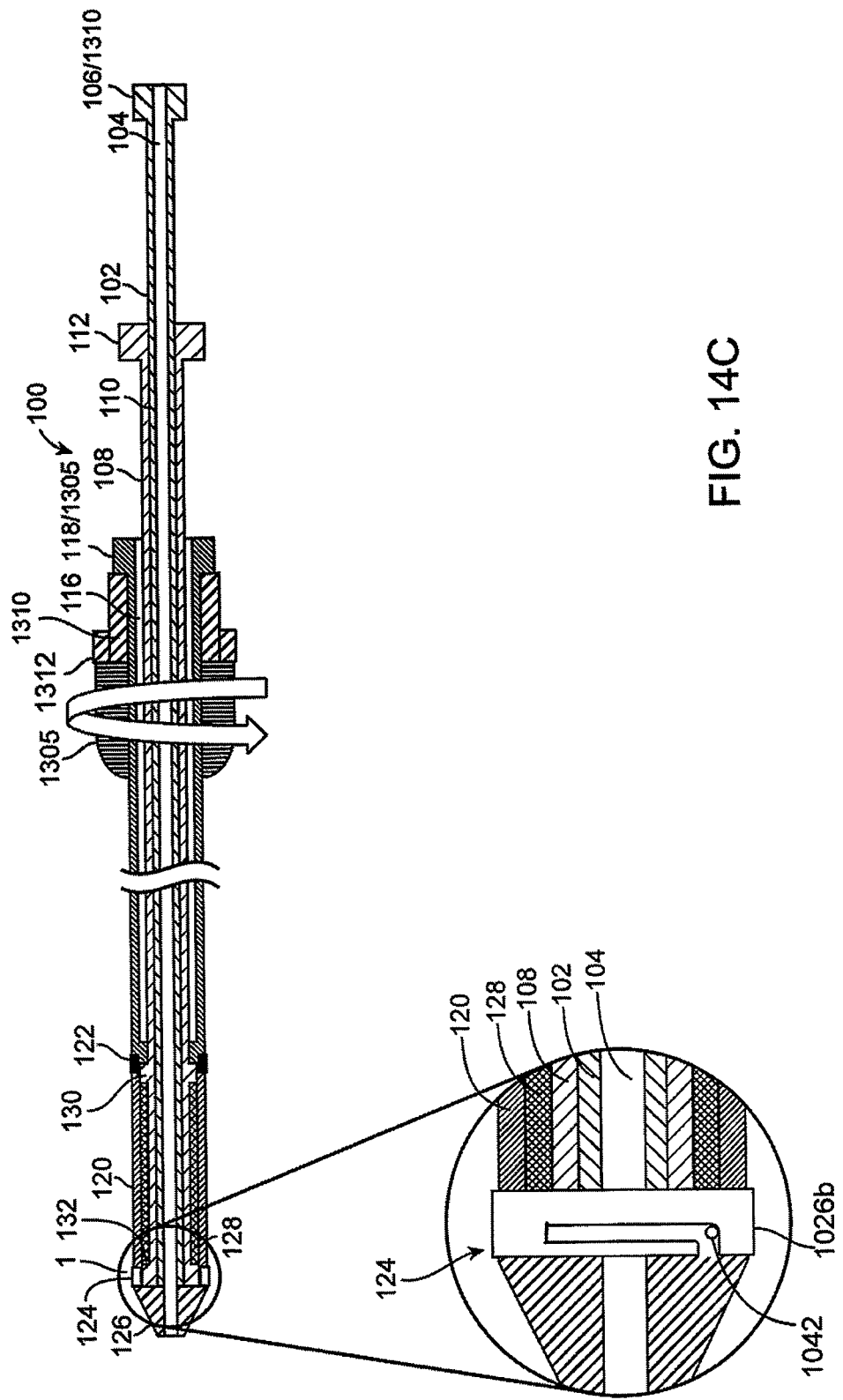

In FIG. 14A, all elements are in their neutral or starting positions, with the pins 1042 at the receiver section (i.e., end 1034b) of the slots 1028b of the female connectors 1026b. In FIG. 14B, the knob 1312 of the selector switch 1310 is pushed in the distal position to allow for distal release. In FIG. 14C, the torquer 1305 is rotated in the clockwise direction as indicated by the arrow. As best seen in insert 1 of FIG. 14C, the pin 1042 travels from the receiver section 1034b, through the transverse section 1032b. The torquer 1305 rotation ends when the pin 1042 rests at the transition between the transverse 1032b and longitudinal 1030b sections of the slot 1028b. The placement of the pin 1042 at the elbow of the slot decouples the distal connectors 124 (illustrated in white) while the proximal connectors 122 (illustrated in black) remain coupled.

Figure 14D:
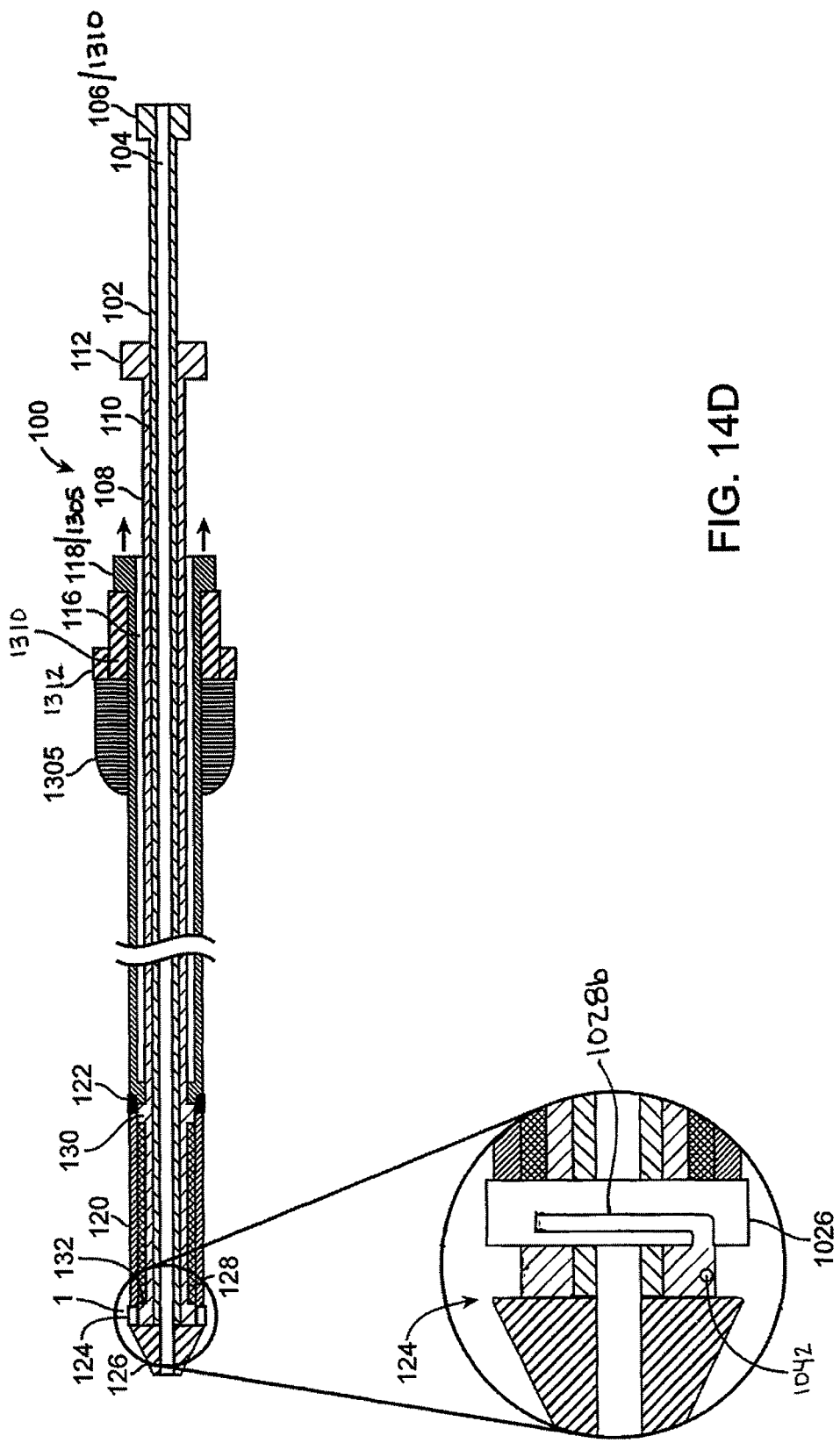

In FIG. 14D, the distal slider 1305 is translated in the proximal direction along with the outer shaft 114. The shuttle sheath 120 also translates in the proximal direction because the shuttle sheath 120 is coupled to the outer shaft 114 via the proximal connectors 122 and not coupled to the nose cone 126 via the distal connectors 124. As best seen in the insert 1 of FIG. 14D, the pin 1042 of the distal connector 124 has traveled through and exited the longitudinal section 1030b of the slot 1028b of the female connector 1026b. As discussed above with regard to FIGS. 10F to 10M, one or more pins 1042 may be connected to or formed in a male connector. Alternative pin 1042 connections and locations are possible. Pin 1042 could be part of a connector or, alternatively, one or more pins 1042 may be integrated into another component, such as the nose cone or a shaft. In the embodiment of FIG. 14, the pin 1042 is connected to or formed from the mid shaft 108.

Figure 14E:
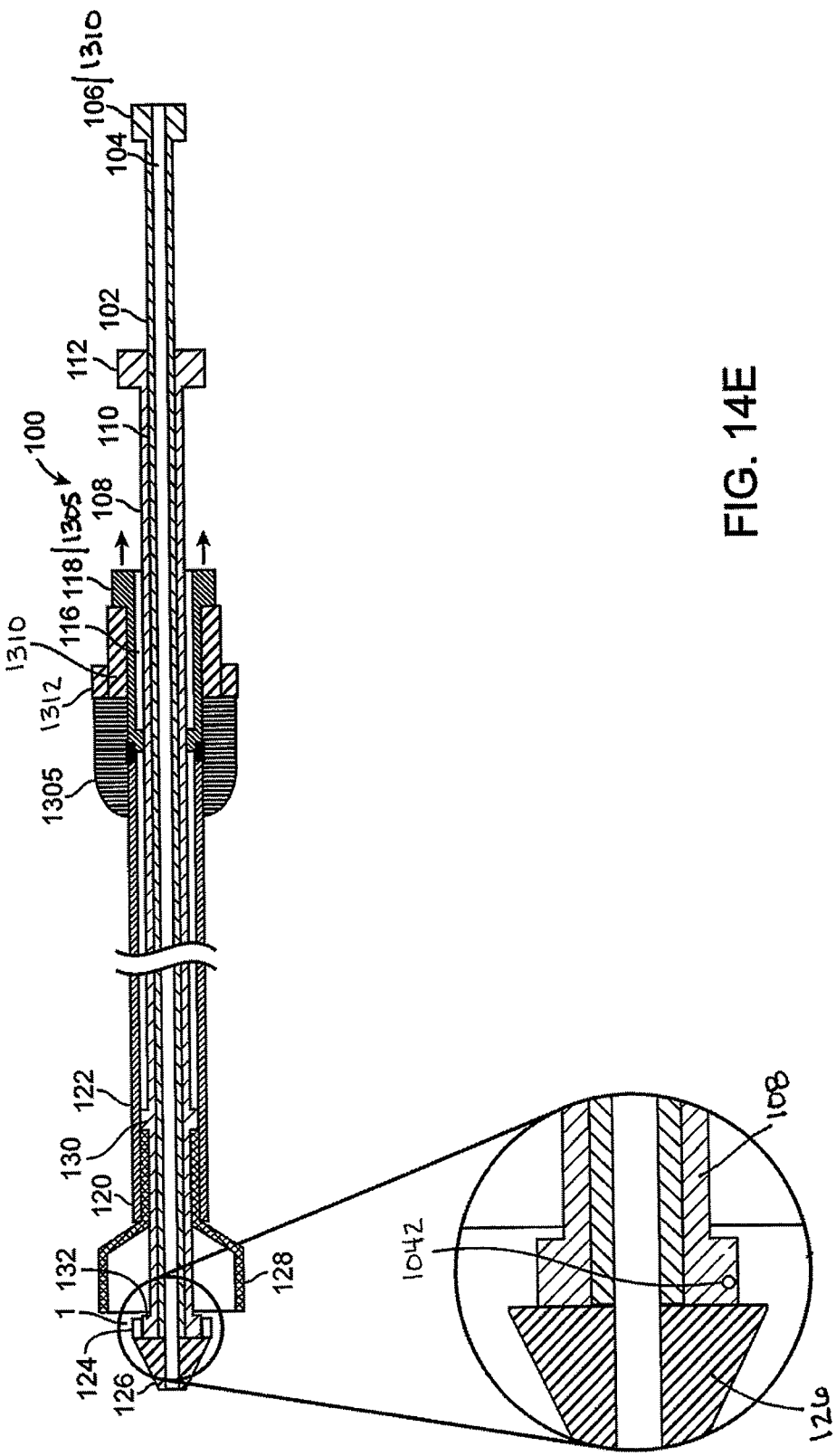
Figure 14F:
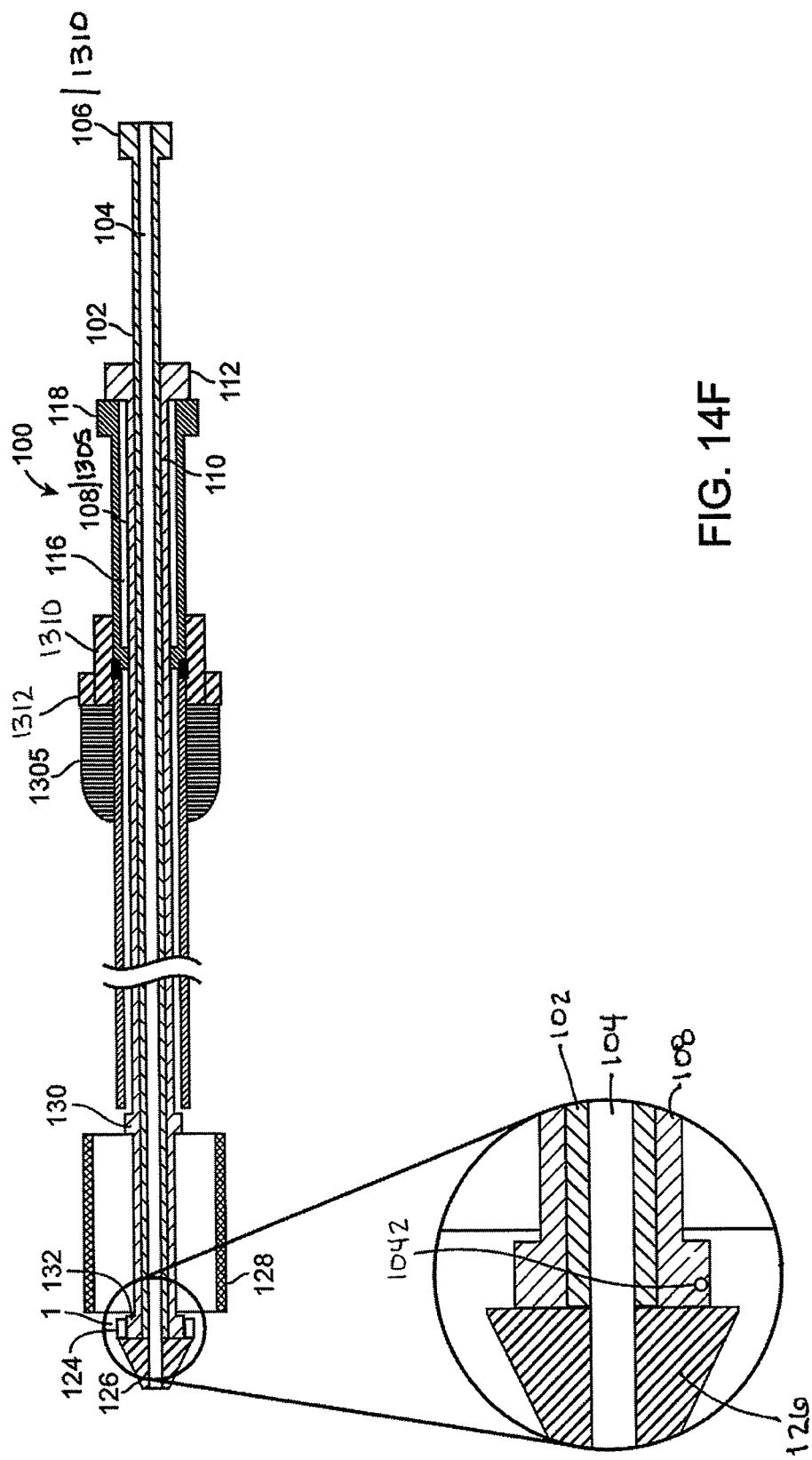

In FIG. 14E, continued translation of the distal slider 1305/hub 118 in the proximal direction partially deploys the stent 128 from the shuttle sheath 120. In FIG. 14F, complete translation of the distal slider 1305/hub 118 in the proximal direction fully deploys the stent 128 from the shuttle sheath 120.

Similar to how FIGS. 14A-14F illustrated stent delivery with regard to FIGS. 1A-D, FIGS. 15A-15F illustrate the proximal release stent deployment of the bi-directional delivery system with regard to the deployment sequence of FIGS. 2A-2D. Enlarged inserts 1 and 2 are again used to show the details of pin and component movement. Additional details in this sequence are used to describe the decoupling of a coupling mechanism with the proximal connectors starting from a pre-connected, locked or engaged state.

Figure 15A:
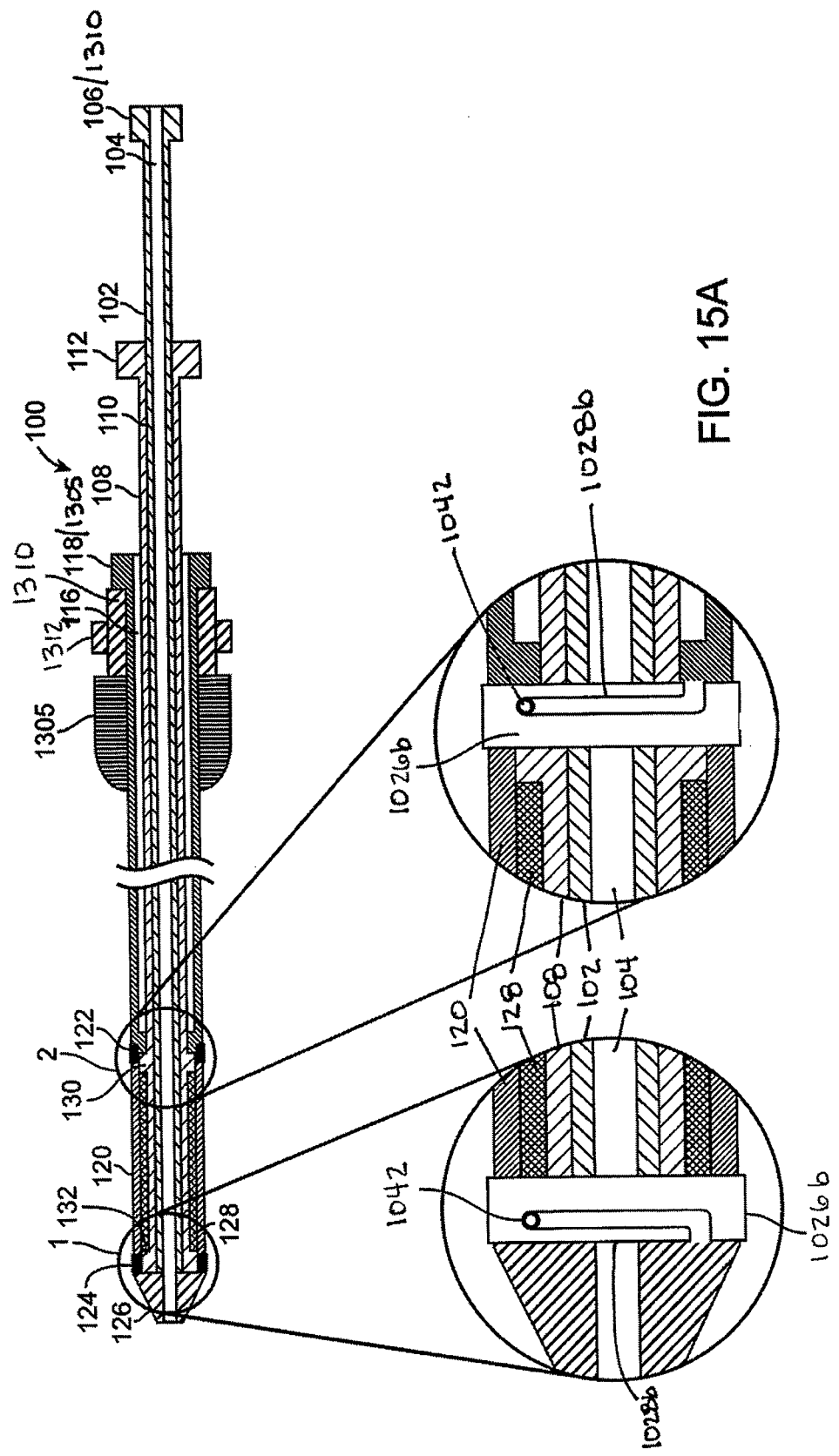
Figure 15C:
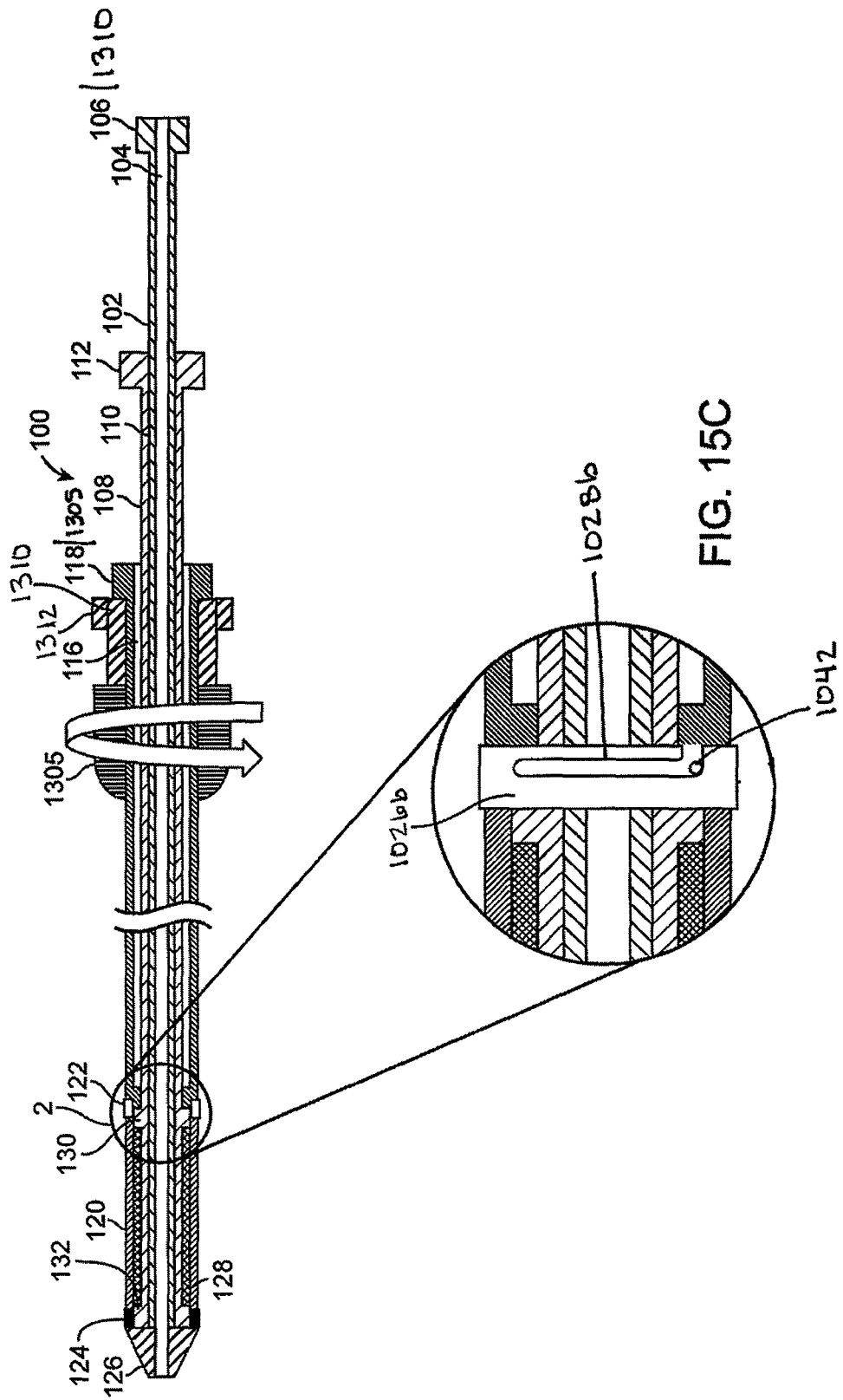
Figure 15D:
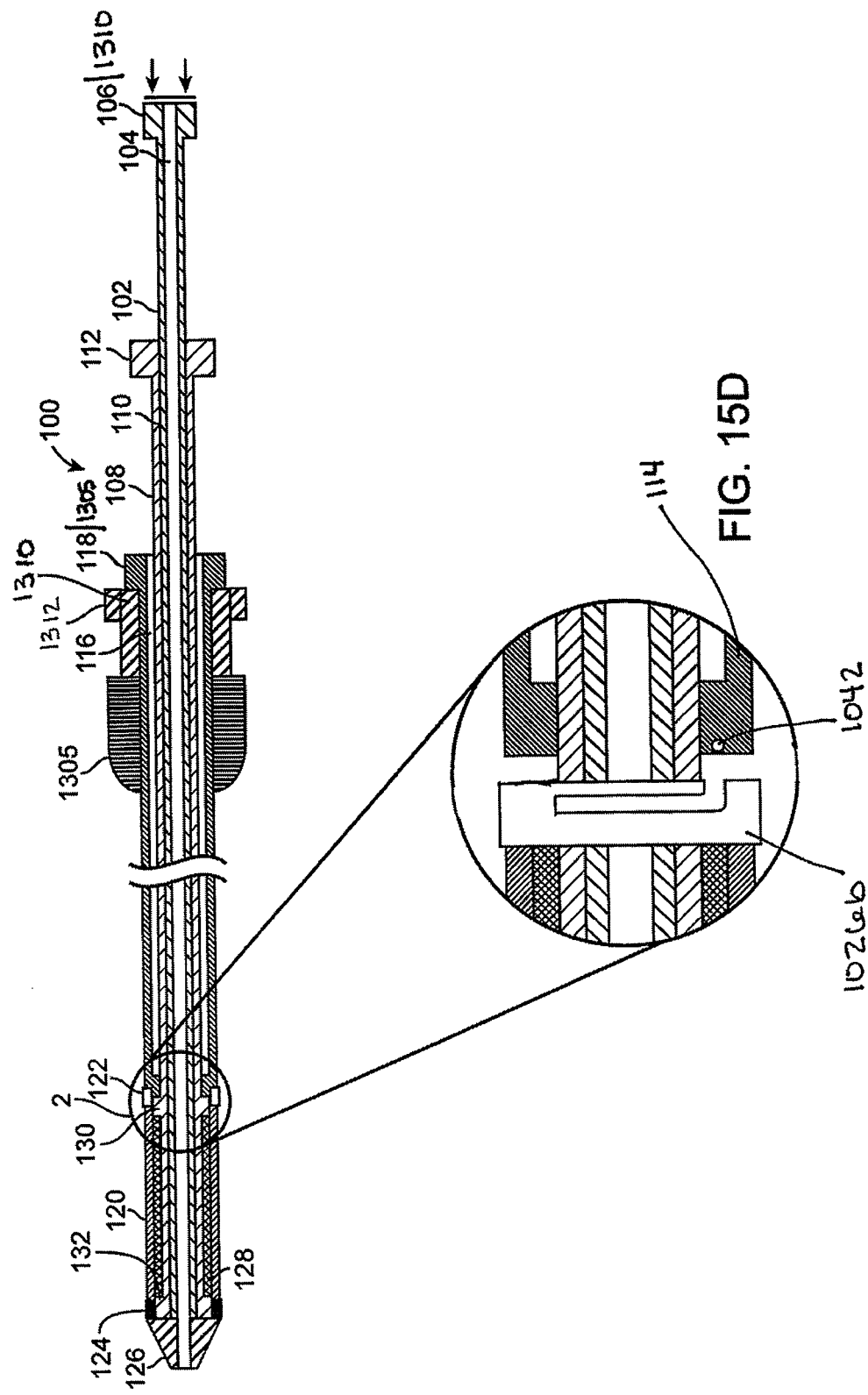
Figure 15E:
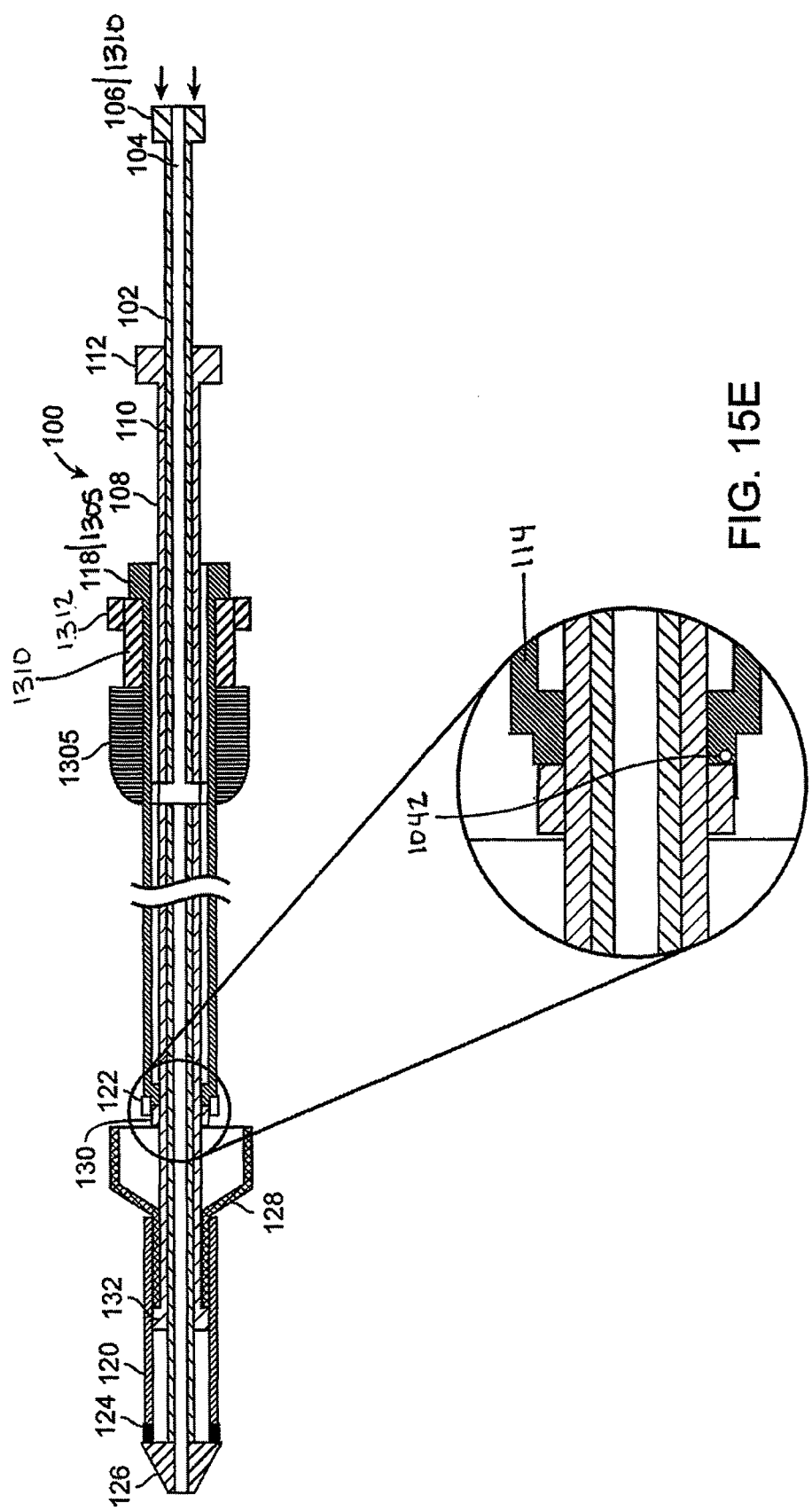

In FIG. 15A, all elements are in their neutral or starting positions, with the pins 1042 of connectors 124, 122 at the receiver section (ends 1034b) of the slots 1028b of female connectors 1026b identical to FIG. 14A and shown in inserts 1 and 2. In FIG. 15B, the knob 1312 of the selector switch 1310 is pushed in the proximal position to allow for proximal release. In FIG. 15C, the torquer 1305 is rotated in the counter-clockwise direction (indicated by the arrow) and the pin 1042 of proximal connector 122 travels from the receiver section 1034b through the transverse section 1032b of the slot 1028b of distal female connector 1026b. At the end of torquer rotation, the pin 1042 rests at the transition between the transverse 1032b and longitudinal 1030b sections of the slot 1028b. The placement of the pin 1042 at the elbow of the slot 1028b decouples the proximal connectors 122 (illustrated in white) while the distal connectors 1241 (illustrated in black) remain coupled. In FIG. 15D, the proximal slider (not shown but coupled to inner hub 106) is translated in the distal direction along with the inner shaft 104. The shuttle sheath 120 also translates in the distal direction because the inner shaft 104 is attached to the nose cone 126, the nose cone 126 is coupled with the shuttle sheath 120 via the still locked distal connectors 124, and the shuttle sheath is disconnected from the outer shaft 108 via the opened proximal connectors 122. The pin 1042 of proximal connector 122 travels through and exits the longitudinal section 1030b of the slot 1028b of distal female connector 1026b. In FIG. 15E, continued translation of the proximal slider/hub 106 in the distal direction partially deploys the stent 128 from the shuttle sheath 120. In FIG. 15F, complete translation of the proximal slider/hub 106 in the distal direction fully deploys the stent 128 from the shuttle sheath 120.

Figure 6A:
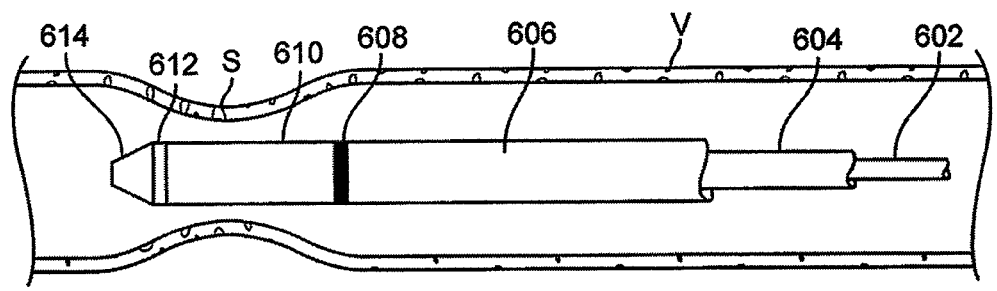
FIGS. 6A-6C illustrate an exemplary method of stenting a vessel with distal stent release.
Figure 6B:
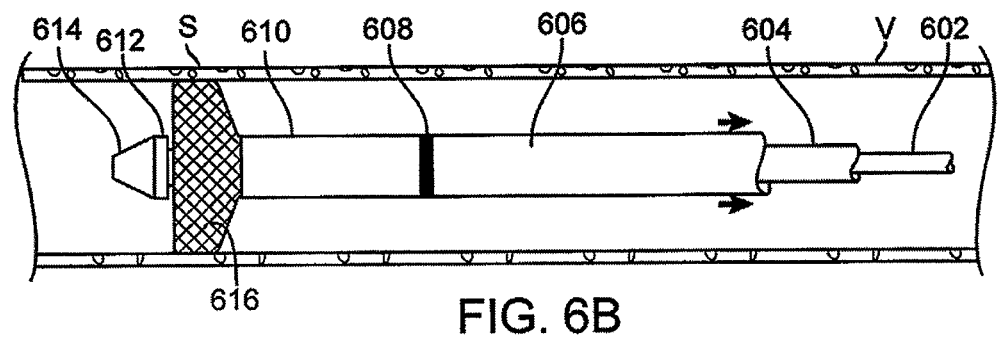
Figure 6C:
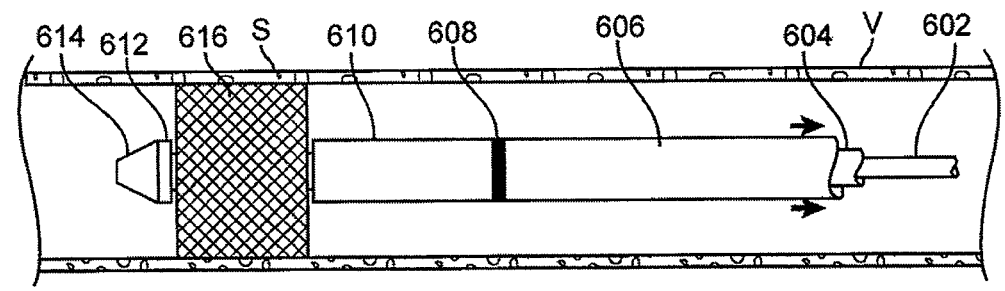

FIGS. 6A-6C illustrate an exemplary method of treating a vessel with a bi-directional stent delivery system such as those described above. In FIG. 6A, the delivery catheter is advanced to a target treatment site in a vessel V. In this embodiment the treatment site is a stenotic region S of a vein caused by compression from surrounding vessels, bone, or other anatomical structures. The delivery catheter includes an inner shaft 602, middle shaft 604, outer shaft 606, shuttle sheath 610, and proximal lock 608, distal lock 612, and nose cone 614. Other aspects of the catheter such as the proximal hubs on the shafts have been omitted for clarity. The proximal lock 608 is shown in the locked position (shown with darkened rectangle), while the distal lock is shown in the unlocked configuration (shown by the white rectangle). Once the catheter is advanced to the target treatment site, the outer sheath is proximally retracted which also proximally retracts the shuttle sheath 610. The stent 616 is then permitted to self expand in the proximal direction, as seen in FIG. 6B until is fully expands into its radially expanded configuration which engages the vessel walls and alleviates the stenosis caused by the compression, as seen in FIG. 6C. The delivery catheter is then removed from the patient. In this exemplary method, as well as others described herein, the delivery catheter may be introduced percutaneously into the vessel and advanced transluminally over a guidewire, such as an 0.035" guidewire. Alternatively, the catheter may be introduced via a surgical cutdown.

Figure 7A:
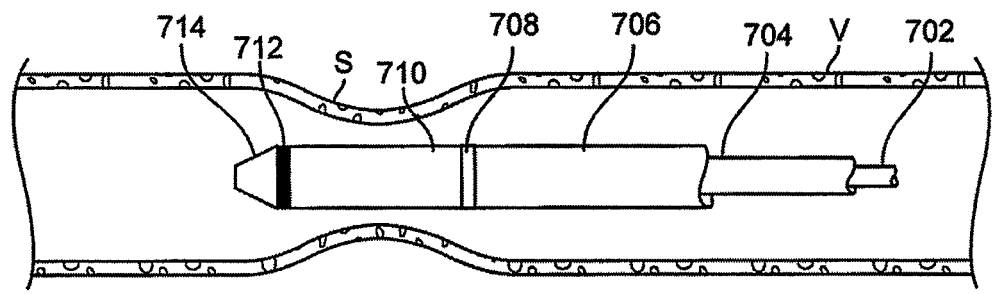
FIGS. 7A-7C illustrate an exemplary method of stenting a vessel with proximal stent release.
Figure 7B:
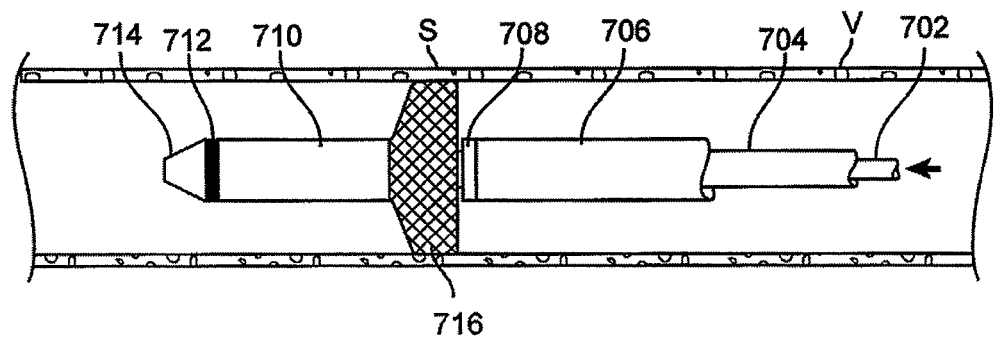
Figure 7C:
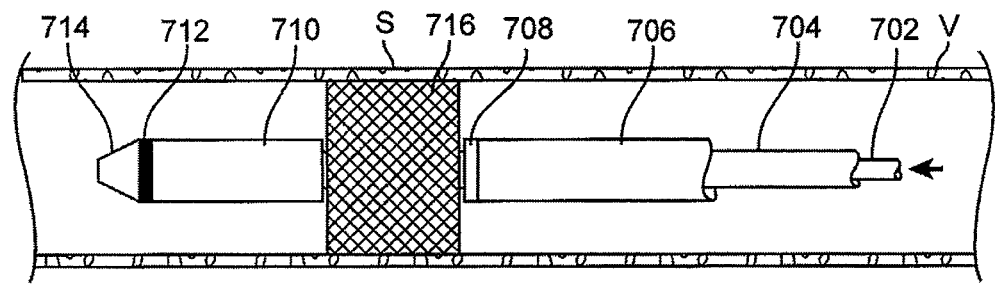

FIGS. 7A-7C illustrate another exemplary method of treating a vessel with the bi-directional stent delivery system such as those previously described above. In FIG. 7A the delivery catheter is advanced to a target treatment site in a vessel V. In this embodiment the treatment site is a stenotic region S of a vein caused by compression from surrounding vessels, bone, or other anatomical structures. The delivery catheter includes an inner shaft 702, middle shaft 704, outer shaft 706, shuttle sheath 710, proximal lock 708, distal lock 712, and nose cone 614. Other aspects of the delivery catheter, such as the proximal hubs have been omitted for clarity. The proximal lock 708 is shown in the unlocked configuration (shown by the white rectangle), while the distal lock 712 is shown in the locked configuration (shown by the darkened rectangle). Once the catheter is advanced to the target treatment site, the inner shaft is advanced distally, thereby also advancing the shuttle sheath 710. The stent 716 becomes unconstrained and self expands in the distal direction, as seen in FIG. 7B until it fully expands into its radially expanded configuration which engages the vessel walls and alleviates the stenosis caused by the compression, as illustrated in FIG. 7C. The delivery catheter is then removed from the patient.

Figure 8A:
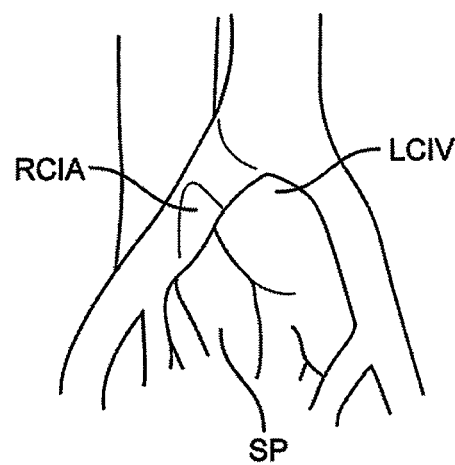
FIGS. 8A-8B illustrate the basic anatomy of iliac vein compression syndrome.
Figure 8B:
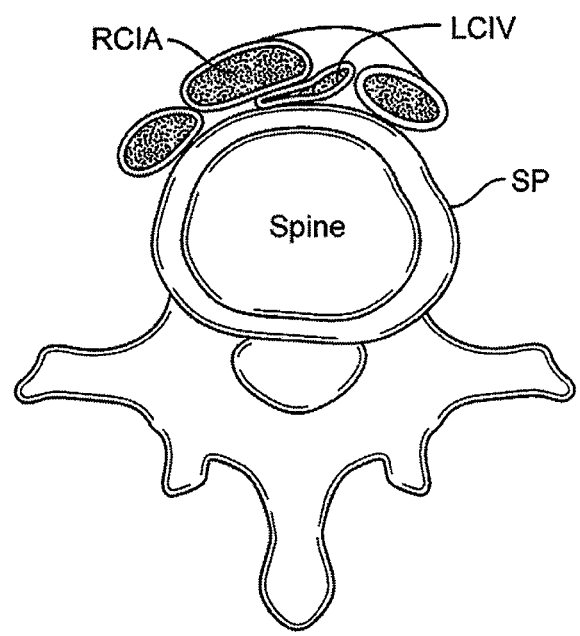

FIGS. 8A-8B illustrate exemplary stenting of a vein as a treatment for venous stenosis. Venous stenosis may be caused by clotting, scarring following blood clots or by focal external compressive forces on a venous vessel (such as in the femoral vein where it crosses the inguinal ligament or in the pelvic vein where it is crossed by overlaying pelvic arteries). The stent or stents may be delivered to the vein using any of the embodiments described above. FIGS. 8A-8B illustrate a vein experiencing external compressive forces. In FIG. 8A the right common iliac artery RCIA is nested against the left common iliac vein LCIV. The spine SP is posterior to both vessels RCIA, LCIV, therefore the left common iliac vein LCIV may be pinched in between a portion of the right common iliac artery RCIV and the spine SP. FIG. 8B illustrates a cross section of FIG. 8A and highlights the pinched portion of the left common iliac vein LCIV. Pinching of the vein obstructs venous outflow. Venous outflow obstruction of the iliac vein, the common outflow tract of the lower limb, can result in severe clinical symptoms. Obstruction of the iliac veins can be attributed to thrombus formation or from external compression from the overlying arterial tree, with possible additional pressure extending from the spine. Venous outflow obstruction is a clinically relevant contributor to chronic venous disease. When combined with venous reflux, outflow obstruction can lead to venous hypertension and the most severe symptoms associated with advanced venous disease such as swelling, discoloration, claudication and ulceration.

Treatment has traditionally been by surgical bypass. However, in the past decade, percutaneous endovenous stenting has emerged as the method of choice in treating venous outflow obstruction due to chronic venous disease. However, there are currently no FDA approved stents or delivery systems for this treatment, and therefore such use is considered off label use. The placement of stents has also proven useful to relieve obstruction that has been revealed after removal of acute iliofemoral thrombus, after a DVT or from obstruction that has been caused by malignant tumors or retroperitoneal thrombosis.

Figure 9:
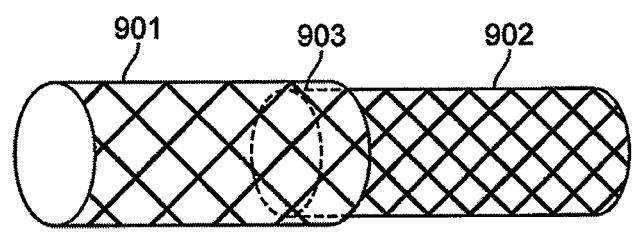
FIG. 9 illustrates overlapping of two or more stents.

Stenting of the vein alleviates the pinch point, thereby permitting normal venous outflow. One or more stents may be placed in the vein. In cases where multiple stents are deployed, the stents may be placed end-to-end, or the stents may be overlapped with one another. FIG. 9 illustrates how two stents 901, 902 may have a region 903 where the two stents overlap with one another. In this embodiment, stent 902 is radially expanded such that a portion of the stent expands into the other stent 901. Overlapping of stents is discussed in greater detail in U.S. patent application Ser. No. 12/903,056, previously incorporated by reference. The stents in this embodiment or those described elsewhere in this specification may also include a therapeutic agent such as an anti-thrombogenic such as heparin, a thrombolytic agent, or another therapeutic agent for reducing blood clots or for another therapy.

In any of the exemplary methods described herein, after the stent or stents have been deployed in the vessel or target treatment site, they may be post-dilated using a balloon catheter in order to tack the stents into the tissue and maximize their expanded diameter. This may be performed with a separate balloon dilatation catheter, or a balloon or other expandable member may be included with embodiments of the delivery system disclosed herein. Positioning and expansion of stents may be verified using intravascular ultrasound (IVUS). The IVUS catheter may be a separate catheter or it may be integrated into the present delivery system. In some embodiments, the IVUS probe is integrated into a standard guidewire, such as an 0.035" guidewire, therefore a conventional guidewire is replaced by the IVUS guidewire.

Although the exemplary embodiments have been described in some detail for clarity of understanding and by way of example, a variety of additional modifications, adaptations and changes may be clear to those of skill in the art. One of skill in the art will appreciate that the various features described herein may be combined with one another or substituted with one another. Hence, the scope of the present invention is limited solely by the appended claims.

INCORPORATION BY REFERENCE

All publications and patent applications mentioned in this specification are herein incorporated by reference to the same extent as if each individual publication or patent application was specifically and individually indicated to be incorporated by reference.

What is claimed is:
1. A bi-directional stent delivery system, said system comprising:
   an elongated inner shaft having a proximal portion and a distal portion;
   a radially expandable prosthesis disposed over the inner shaft, the prosthesis having a radially collapsed configuration and a radially expanded configuration, wherein in the collapsed configuration the prosthesis is adapted to be delivered through a vasculature, and in the expanded configuration the prosthesis engages a vessel wall;
an elongated outer shaft having a proximal portion and a distal portion; and
a shuttle sheath having a proximal portion and a distal portion, the shuttle sheath disposed over the radially expandable prosthesis, the distal portion of the shuttle sheath releasably lockable to the distal portion of the inner shaft via a distal coupling mechanism, and the proximal portion of the shuttle sheath releasably lockable to the distal portion of the outer shaft via a proximal coupling mechanism,
wherein the stent delivery system is configured to be selectively actuated between a proximal deployment configuration and a distal deployment configuration, when the stent delivery system is in the proximal deployment configuration, the shuttle sheath is locked with the inner shaft and unlocked from the outer shaft such that distal advancement of the inner shaft advances the shuttle sheath distally relative to the outer shaft, thereby allowing the prosthesis to radially expand from a proximal end thereof to a distal end thereof, and
when the stent delivery system is in the distal deployment configuration, the shuttle sheath is unlocked from the inner shaft and locked with the outer shaft such that proximal retraction of the outer shaft retracts the shuttle sheath proximally relative to the inner shaft, thereby allowing the prosthesis to radially expand from the distal end thereof to the proximal end thereof.

2. The system of claim 1, wherein the shuttle sheath constrains the prosthesis such that a portion of the prosthesis disposed under a portion of the shuttle sheath is constrained in the radially collapsed configuration at least until the portion of the shuttle sheath is removed from over the portion of the prosthesis to allow to the prosthesis to radially expand to the radially expanded configuration.

3. The system of claim 1, wherein the distal coupling mechanism comprises a bayonet coupling.

4. The system of claim 3, the bayonet coupling further comprising a male connector with at least one pin and a female connector having a slot configured to receive the at least one pin.

5. The system of claim 4 wherein the slot comprises a linear section and a transverse section that extends from the linear section in an orientation transverse to an orientation of the linear section.

6. The system of claim 5 wherein the transverse section is oriented at a 90 degree angle from the orientation of the linear section.

7. The system of claim 5, wherein the slot further comprises a receiver section that extends from the transverse section, the receive section including a flared end having a diameter that is greater than a diameter of each of the linear section and the transverse section.

8. The system of claim 5, wherein the transverse section is oriented at about a 45 degree angle from the orientation of the linear section.

9. The system of claim 5, wherein the transverse section is oriented at an angle between 60 and 150 degrees relative to the orientation of the linear section.

10. The system of claim 4 wherein the width of the slot is narrowed at one portion so as to form a friction fit with the at least one pin.

11. The system of claim 4 wherein the female connector has two or more slots of similar configuration with the two or more slots arranged equidistant from one another around the circumference of the female connector.

12. The system of claim 4, wherein the slot extends through a sidewall of the female connector.

13. The system of claim 4, wherein the slot comprises a transverse section that curves along an arc of about 90 degrees.

14. The system of claim 4, wherein the male connector is disposed on one of the shuttle sheath or the inner shaft, and the female connector is disposed on the other of the shuttle sheath or the inner shaft.

15. The system of claim 4, wherein the at least one pin is disposed directly on at least one of the inner shaft or a middle shaft that is slidably disposed over the inner shaft and within the outer shaft.

16. The system of claim 1, wherein the distal coupling mechanism comprises a threaded region on the distal portion of the inner shaft and a corresponding threaded region on the distal portion of the shuttle sheath.

17. The system of claim 1, wherein the distal coupling mechanism comprises a helical region on the distal portion of the inner shaft and a corresponding helical region on the distal portion of the shuttle sheath.

18. The system of claim 1, wherein the distal coupling mechanism comprises one or more of a snap fit, an interference fit, a barbed connector, a locking mechanism, a rotatable key lock, a linear key lock, a threaded bushing, a twist lock, a magnetic coupling, or a frangible connector.

19. The system of claim 1, wherein the proximal coupling mechanism comprises a bayonet coupling.

20. The system of claim 1, wherein the proximal coupling mechanism comprises a threaded region on the distal portion of the outer shaft and a corresponding threaded region on the proximal portion of the shuttle sheath.

21. The system of claim 1, wherein the proximal coupling mechanism comprises a helical region on the distal portion of the outer shaft and a corresponding helical region on the proximal portion of the shuttle sheath.

22. The system of claim 1, wherein the proximal coupling mechanism comprises one or more of a snap fit, an interference fit, a barbed connector, a locking mechanism, a rotatable key lock, a linear key lock, a threaded bushing, a twist lock, a magnetic coupling, or a frangible connector.

23. The system of claim 1, wherein the distal coupling mechanism is a first bayonet coupling mechanism having a first slot in a first orientation, and the proximal coupling mechanism is a second bayonet coupling mechanism having a second slot in a second orientation opposite the first orientation of the first slot, and wherein rotation of the inner shaft in a first direction locks the first bayonet coupling mechanism and rotation of the inner shaft in a second direction opposite the first direction unlocks the first bayonet coupling mechanism, and wherein rotation of the outer shaft in the first direction unlocks the second bayonet coupling mechanism and rotation of the outer shaft in the second direction locks the second bayonet coupling mechanism.

24. The system of claim 23 wherein each of the first and second slots comprises a linear section, a transverse section and a receiver section.

25. The system of claim 24 wherein the transverse section is oriented at a 90 degree angle from an orientation of the linear section.

26. The system of claim 23 wherein the width of each of the first and second slots is narrowed at one portion so as to form a friction fit with a portion of the respective coupling mechanism.

27. The system of claim 26 wherein the portion of the respective coupling mechanism is a pin.

28. The system of claim 1, wherein the distal portion of the inner shaft is coupled to a nosecone, the distal coupling mechanism releasably locks the distal end of the shuttle sheath with the distal end of the inner shaft via the nosecone.

29. The system of claim 1, wherein the distal coupling mechanism is a left-handed bayonet coupling, and the proximal coupling mechanism is a right-handed bayonet coupling.

30. The system of claim 1, further comprising a handle coupled to the inner shaft and the outer shaft, the handle including a longitudinal body and a torquer that is rotatable relative to the body, wherein rotation of the torquer in one direction causes rotation of at least one of the outer shaft or the inner shaft in the same direction.

31. The system of claim 30, wherein the torquer is configured to selectively lock and unlock the distal portion of the outer shaft to the proximal portion of the shuttle sheath via the proximal coupling mechanism.

32. The system of claim 30, wherein the torquer is configured to selectively lock and unlock the distal portion of the shuttle sheath to the distal portion of the inner shaft via the distal coupling mechanism.

33. The system of claim 30, further comprising a selector switch on the handle that determines a direction that the torquer is allowed to rotate relative to the body of the handle, the selector switch being movable between a first position and a second position.

34. The system of claim 33, wherein the stent delivery system is selectively actuated between the proximal deployment configuration and the distal deployment configuration by moving the selector switch between the first and second positions.

35. The system of claim 33, wherein when the selector switch is in the first position the torquer is allowed to rotate in a clockwise direction only, and when the selector switch is in the second position the torquer is allowed to rotate in a counterclockwise direction only.

36. The system of claim 35, wherein rotation of the torquer in the clockwise direction when the selector switch is in the first position unlocks the distal coupling mechanism between the inner shaft and the shuttle sheath while retaining the proximal coupling mechanism in a locked state such that proximal retraction of the outer shaft retracts the shuttle sheath proximally relative to the inner shaft, allowing the prosthesis to radially expand from the distal end to the proximal end thereof.

37. The system of claim 35, wherein rotation of the torquer in the counterclockwise direction when the selector switch is in the second position unlocks the proximal coupling mechanism between the outer shaft and the shuttle sheath while retaining the distal coupling mechanism in a locked state such that distal advancement of the inner shaft advances the shuttle sheath distally relative to the outer shaft, allowing the prosthesis to radially expand from the proximal end to the distal end thereof.

38. The system of claim 30, further comprising a distal slider disposed on the body of the handle, the distal slider coupled to the outer shaft such that proximal movement of the distal slider relative to the body produces proximal movement of the outer shaft relative to the inner shaft.

39. The system of claim 38, wherein the body of the handle includes threads, the distal slider configured to rotate on the threads of the body in a first mode of operation to provide fine translation of the outer shaft in at least one of a proximal direction or a distal direction relative to the inner shaft.

40. The system of claim 39, wherein the distal slider includes a release button, the distal slider configured to decouple from the threads of the body when the release button is actuated to allow the distal slider to translate along the body in a second mode of operation to provide rapid translation of the outer shaft in at least one of the proximal or distal directions.

41. The system of claim 30, further comprising a proximal slider disposed on the body of the handle, the proximal slider coupled to the inner shaft such that distal movement of the proximal slider relative to the body produces distal movement of the inner shaft relative to the outer shaft.

42. The system of claim 41, wherein the body of the handle includes threads, the proximal slider configured to rotate on the threads of the body in a first mode of operation to provide fine translation of the inner shaft in at least one of a proximal direction or a distal direction relative to the outer shaft.

43. The system of claim 42, wherein the proximal slider includes a release button, the proximal slider configured to decouple from the threads of the body when the release button is actuated to allow the proximal slider to translate along the body in a second mode of operation to provide rapid translation of the inner shaft in at least one of the proximal or distal directions.

44. A bi-directional stent delivery system comprising:
an elongated inner shaft having a proximal portion and a distal portion;
a radially expandable prosthesis disposed over the inner shaft, the prosthesis having a radially collapsed configuration and a radially expanded configuration, wherein in the collapsed configuration the prosthesis is adapted to be delivered through a vasculature, and in the expanded configuration the prosthesis engages a vessel wall;
an elongated outer shaft having a proximal portion and a distal portion;
a shuttle sheath having a proximal portion and a distal portion, the shuttle sheath disposed over the radially expandable prosthesis, the distal portion of the shuttle sheath releasably lockable to the distal portion of the inner shaft via a distal coupling mechanism, and the proximal portion of the shuttle sheath releasably lockable to the distal portion of the outer shaft via a proximal coupling mechanism; and
a handle including a longitudinal body and a torquer that is rotatable relative to the body, wherein rotation of the torquer in one direction causes rotation of at least one of the outer shaft or the inner shaft in the same direction, wherein rotation of the torquer is used to selectively lock and unlock at least one of the distal coupling mechanism or the proximal coupling mechanism,
wherein the stent delivery system is configured to be selectively actuated between a proximal deployment configuration and a distal deployment configuration by moving a selector switch on the handle between first and second positions, the first and second positions of the selector switch each allow the torquer to rotate relative to the body in only one direction, and the direction of rotation of the torquer determines the locking and unlocking of the respective distal and proximal coupling mechanisms.

45. The system of claim 44, wherein the stent delivery system is configured to, when the stent delivery system is in the proximal deployment configuration, lock the shuttle sheath with the inner shaft and unlock the shuttle sheath from the outer shaft such that distal advancement of the inner shaft advances the shuttle sheath distally relative to the outer shaft, thereby allowing the prosthesis to radially expand from a proximal end thereof to a distal end thereof, and when the stent delivery system is in the distal deployment configuration, and configured to unlock the shuttle sheath from the inner shaft and lock the shuttle sheath with the outer shaft such that proximal retraction of the outer shaft retracts the shuttle sheath proximally relative to the inner shaft, thereby allowing the prosthesis to radially expand from the distal end thereof to the proximal end thereof.

46. The system of claim 44, wherein when the selector switch is in the first position the torquer is allowed to rotate in a clockwise direction only, and when the selector switch is in the second position the torquer is allowed to rotate in a counterclockwise direction only.

47. The system of claim 46, wherein rotation of the torquer in the clockwise direction when the selector switch is in the first position unlocks the distal coupling mechanism between the inner shaft and the shuttle sheath while retaining the proximal coupling mechanism in a locked state such that proximal retraction of the outer shaft retracts the shuttle sheath proximally relative to the inner shaft, allowing the prosthesis to radially expand from the distal end to the proximal end thereof.

48. The system of claim 46, wherein rotation of the torquer in the counterclockwise direction when the selector switch is in the second position unlocks the proximal coupling mechanism between the outer shaft and the shuttle sheath while retaining the distal coupling mechanism in a locked state such that distal advancement of the inner shaft advances the shuttle sheath distally relative to the outer shaft, allowing the prosthesis to radially expand from the proximal end to the distal end thereof.

49. The system of claim 44, further comprising a distal slider disposed on the body of the handle, the distal slider coupled to the outer shaft such that proximal movement of the distal slider relative to the body produces proximal movement of the outer shaft relative to the inner shaft.

50. The system of claim 49, wherein the body of the handle includes threads, the distal slider configured to rotate on the threads of the body in a first mode of operation to provide fine translation of the outer shaft in at least one of a proximal direction or a distal direction relative to the inner shaft.

51. The system of claim 50, wherein the distal slider includes a release button, the distal slider configured to decouple from the threads of the body when the release button is actuated to allow the distal slider to translate along the body in a second mode of operation to provide rapid translation of the outer shaft in at least one of the proximal or distal directions.

52. The system of claim 44, further comprising a proximal slider disposed on the body of the handle, the proximal slider coupled to the inner shaft such that distal movement of the proximal slider relative to the body produces distal movement of the inner shaft relative to the outer shaft.

53. The system of claim 52, wherein the body of the handle includes threads, the proximal slider configured to rotate on the threads of the body in a first mode of operation to provide fine translation of the inner shaft in at least one of a proximal direction or a distal direction relative to the outer shaft.

54. The system of claim 53, wherein the proximal slider includes a release button, the proximal slider configured to decouple from the threads of the body when the release button is actuated to allow the proximal slider to translate along the body in a second mode of operation to provide rapid translation of the inner shaft in at least one of the proximal or distal directions.

55. The system of claim 44, wherein the distal coupling mechanism is a bayonet coupling, the bayonet coupling including at least one pin on one of the distal portion of the inner shaft or the distal portion of the shuttle sheath, the bayonet coupling further including at least one slot that is configured to receive the at least one pin on the other of the distal portion of the inner shaft or the distal portion of the shuttle sheath.

56. The system of claim 55, wherein rotation of the torquer causes movement of the at least one pin relative to the at least one slot to selectively lock and unlock the distal coupling mechanism.

57. The system of claim 55, wherein the at least one slot comprises a linear section and a transverse section that extends from the linear section in an orientation transverse to an orientation of the linear section.

58. The system of claim 57, wherein the transverse section is oriented at an angled between 60 and 150 degrees relative to the orientation of the linear section.

59. The system of claim 58, wherein the transverse section is oriented at a 90 degree angle from the orientation of the linear section.

60. The system of claim 57, wherein the transverse section is oriented at about a 45 degree angle from the orientation of the linear section.

61. The system of claim 57, wherein the at least one slot further comprises a receiver section that extends from the transverse section, the receiver section including a flared end having a diameter that is greater than a diameter of each of the linear section and the transverse section, the receiver section configured to receive the at least one pin to lock the distal coupling mechanism.

62. The system of claim 44, wherein the proximal coupling mechanism is a bayonet coupling, the bayonet coupling including at least one pin on one of the distal portion of the outer shaft or the proximal portion of the shuttle sheath, the bayonet coupling further including at least one slot that is configured to receive the at least one pin on the other of the distal portion of the outer shaft or the proximal portion of the shuttle sheath.

63. The system of claim 62, wherein rotation of the torquer causes movement of the at least one pin relative to the at least one slot to selectively lock and unlock the proximal coupling mechanism.

64. The system of claim 62, wherein the at least one slot comprises a linear section and a transverse section that extends from the linear section in an orientation transverse to an orientation of the linear section.

65. The system of claim 64, wherein the transverse section is oriented at an angled between 60 and 150 degrees relative to the orientation of the linear section.

66. The system of claim 65, wherein the transverse section is oriented at a 90 degree angle from the orientation of the linear section.

67. The system of claim 64, wherein the transverse section is oriented at about a 45 degree angle from the orientation of the linear section.

68. The system of claim 64, wherein the at least one slot further comprises a receiver section that extends from the transverse section, the receiver section including a flared end having a diameter that is greater than a diameter of each of the linear section and the transverse section, the receiver section configured to receive the at least one pin to lock the proximal coupling mechanism.

69. The system of claim 44, wherein the shuttle sheath constrains the prosthesis such that a portion of the prosthesis disposed under a portion of the shuttle sheath is constrained in the radially collapsed configuration at least until the portion of the shuttle sheath is removed from over the portion of the prosthesis to allow to the prosthesis to radially expand to the radially expanded configuration.

70. The system of claim 44, wherein the distal coupling mechanism is a left-handed bayonet coupling, and the proximal coupling mechanism is a right-handed bayonet coupling such that rotating the torquer in one direction unlocks only one of the distal coupling mechanism or proximal coupling mechanism.

* * * * *